US010925891B2

(12) United States Patent
Baker

(10) Patent No.: US 10,925,891 B2
(45) Date of Patent: Feb. 23, 2021

(54) CARRIER STATUS OF ANNEXIN A5 M2 HAPLOTYPE AND OBSTETRIC RISKS

(71) Applicant: IHG Pharmaco Limited, London (GB)

(72) Inventor: Deborah Jane Baker, Warwickshire (GB)

(73) Assignee: IHG Pharmaco Ltd., London (GB)

( * ) Notice: Subject to any disclaimer, the term of this patent is extended or adjusted under 35 U.S.C. 154(b) by 47 days.

(21) Appl. No.: 15/302,340

(22) PCT Filed: Apr. 7, 2015

(86) PCT No.: PCT/GB2015/051066
§ 371 (c)(1),
(2) Date: Oct. 6, 2016

(87) PCT Pub. No.: WO2015/155523
PCT Pub. Date: Oct. 15, 2015

(65) Prior Publication Data
US 2017/0027981 A1    Feb. 2, 2017

Related U.S. Application Data

(60) Provisional application No. 61/976,223, filed on Apr. 7, 2014, provisional application No. 62/032,099, filed on Aug. 1, 2014, provisional application No. 62/085,672, filed on Dec. 1, 2014, provisional application No. 62/115,230, filed on Feb. 12, 2015.

(51) Int. Cl.
*A61K 31/727* (2006.01)
*C12Q 1/6883* (2018.01)
*A61P 15/06* (2006.01)
*C12Q 1/6876* (2018.01)

(52) U.S. Cl.
CPC ............ *A61K 31/727* (2013.01); *A61P 15/06* (2018.01); *C12Q 1/6876* (2013.01); *C12Q 1/6883* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

WO      2006038037 A2      4/2006
WO      WO 2012/025616   *  3/2012

OTHER PUBLICATIONS

Bates et al. Venous Thromboembolism, Thrombophilia, Antithrombotic Therapy, and Pregnancy: American College of Chest Physicians Evidence-Based Clinical Practice Guidelines (8th Edition). Chest 2008;133;844-886. (Year: 2008).*
Appels et al. Advances in genome studies: the PAG 2010 conference. Funct Integr Genomics (2010) 10:1-9. (Year: 2010).*
Grandone et al., "Role of the M2 haplotype within the annexin A5 gene in the occurrence of pregnancy-related venous thromboembolism" American Journal of Obstetrics and Gynecology vol. 203 pp. 461.e1-461.e5 (Year: 2010).*
Ghosh et al., "Successful Pregnancy Outcome in Women With Bad Obstetric History and Recurrent Fetal Loss Due to Thrombophilia: Effect of Unfractionated Heparin and Low-Molecular Weight Heparin" Clinical and Applied Thrombosis/Hemostasis vol. 14 No. 2 pp. 174-179 (Year: 2008).*
Hayashi, Y. et al., "Genotyping analyses for polymorphisms of ANXA5 gene in patients with recurrent pregnancy loss," Fertility and Sterility, vol. 100: No. 4; (Oct. 2013).
Markoff, A. "Haplotypes and polymorphisms of the ANXA5 nontranslated region in Japanese and European women with recurrent miscarriage andin controls," Fertility and Sterility, vol. 101, No. 1 (Jan. 2014).
Akhtar, M. "Aspirin and Heparin as Adjuvants During IVF Do Not Improve Live Birth Rates in Unexplained Implantation Failure," Reproductive BioMedicine Online (2013) 26, 586-594.
Akhtar, M. et al., "Heparin for Assisted Reproduction: Summary of a Cochrane Review," Fertility and Sterility, vol. 103, No. 1 (2015).
Bogdanova, N. and Markoff, A. "Hereditary Thrombophilic Risk Factors for Recurrent Pregnancy Loss," J. Community Genet. (2010) 1:47-53.
Bogdanova, N. et al., "A Common Haplotype of the Annexin A5 (ANXA5) Gene Promoter is Associated with Recurrent Pregnancy Loss," Human Molecular Genetics, 2007, vol. 16, No. 5.
Bogdanova, N. et al., "The Annexin A5 Protective Shield Model Revisited: Inherited Carriage of the M2/ANXA5 Haplotype in Placenta as a Predisposing Factor for the Development of Obstetric Antiphospholipid Antibodies", Lupus, vol. 21, No. 7, pp. 796-798, (2012).

(Continued)

*Primary Examiner* — Eric Olson
(74) *Attorney, Agent, or Firm* — Michele M. Wales; Inhouse Patent Counsel, LLC

(57) ABSTRACT

The present invention relates to determining the carrier status of Annexin A5 M2 haplotype of parents (both male and female) prior to and/or after pregnancy to minimize the risk of pregnancy complications, including, but not limited to, recurrent pregnancy loss (RPL), infertility, miscarriage, in vitro fertilization (IVF) failure, IUI failure, implantation failure, foetal growth restriction (FGR), small for gestational age (SGA) newborn, intra-uterine foetal death (IUFD), gestational hypertension (GH), pre-eclampsia (PE) and/or venous thromboembolism (VTE). Once M2 carrier status is determined, methods of intervention, including administration of low molecular weight heparin (LMWH) and/or other anti-coagulants can be administered either prior to and/or after pregnancy. Methods of detecting the carrier status as well as method of diagnosing and or predicting prognosis based on the M2 carrier status of a patient and/or couple is also contemplated.

25 Claims, 1 Drawing Sheet
Specification includes a Sequence Listing.

(56) References Cited

OTHER PUBLICATIONS

Brice, P., "Genetic Screening Could Reduce Recurrent Miscarriages", Retrieved from the Internet: URL:http://www.phgfoundation.org/news/16184/, XP055199729, pp. 1-2, (2014).
Bristow, S. et al., "Biomarkers for Infertility and Recurrent Pregnancy Loss", Reproductive Biomedicine Online, vol. 29, No. 1, pp. 1-2, (2014).
Clark et al., "SPIN (Scottish Pregnancy Intervention) study: a multicenter, randomized controlled trial of low-molecular-weight heparin and low-dose aspirin in women with recurrent miscarriage," Blood, May 27, 2010, vol. 115, No. 21.
EPO Examination Report dated Aug. 18, 2017 received in 15 723 547.4.
Fishel, S. et al., "Multicentre Study of the Clinical Relevance of Screening IVF Patients for Carrier Status of the Annexin A5 M2 Haplotype", Reproductive Biomedicine Online, vol. 29, No. 1, pp. 80-87, (2014).
H. Ueki et al., "Loss of Maternal Annexin A5 Increases the Likelihood of Placental Platelet Thrombosis and Foetal Loss", Scientific Reports, vol. 2, XP055199620, DOI: 10.1038/srep00827, (2012).
International Search Report and Written Opinion received in PCT/GB2015/051066, dated Oct. 28, 2015.
Kaandorp, S. et al., "Aspirin plus Heparin or Aspirin Alone in Women with Recurrent Miscarriage," N Engl J Med 2010 (10.1056/NEJMoa1000641).
Nagirnaja, L. et al., "Annexin A5 Promoter Haplotype M2 Is Not a Risk Factor for Recurrent Pregnancy Loss in Northern Europe," PLOS One | DOI:10.1371/journal.pone.0131606 Jul. 2, 2015.

Noci, I. et al. "Effect of Dalteparin Sodium Administration on IVF Outcome in Non-Thrombophilic Young Women:a Pilot Study," Reproductive BioMedicine Online (2011) 22, 615-620.
Rodger, M. et al. "Antepartum Dalteparin Versus No Antepartum Dalteparin for the Prevention of Pregnancy Complications in Pregnant Women With Thrombophilia (TIPPS)", Obstetrical & Gynecological Survey, vol. 70, No. 2, pp. 76-78, (2015).
Rogenhofer, N. et al., "Paternal and Maternal Carriage of Theannexin A5 M2 Haplotype Areequal Risk Factors for Recurrent Pregnancy Loss: A Pilot Study", Fertility and Sterility, Elsevier Science Inc. New York, NY, USA, vol. 98, No. 2, pp. 383-388, (2012).
Seshadri, S. et al., "Effect of heparin on the outcome of IVF treatment: a systematic review and meta-analysis," Reproductive BioMedicine Online (2012) 25, 572-584.
Tan, W et al., "Does Low-Molecular-Weight Heparin Improve Live Birth Rates in Pregnant Women with Thrombophilic Disorders? A Systematic Review," Singapore Med J 2012; 53(10) 660.
The Royal College of Obstetricians & Gynaecologists "The Investigation and Treatment of Couples with Recurrent First-trimester and Second-trimester Miscarriage," Green-top Guideline No. 17 (Apr. 2011).
Third Party Observation for application No. EP20150723547 dated Mar. 21, 2017.
Urman, B. et al., "Luteal Phase Empirical Low Molecular Weight Heparin Administration in Patients with Failed ICSI Embryo Transfer Cycles: A Randomized Open-Labeled Pilot Trial," Human Reproduction, vol. 24, No. 7 pp. 1640-1647, 2009.
Japanese Office Action and English translation dated Jan. 22, 2019 received in corresponding Patent Application No. 2016-561849.

* cited by examiner

```
  1 CCGAGCCCTG GACAGCTCCC CAGGCCCTTC CCGCGGCGCG AGGACAAGAG

-202
 51 GTC|TCCGGGG CCCTCGGGGG AGCGGCGCCT CCTCCTGGTT CCAGCAGCTC

101 TGCGGCCGCT CCCCACCCAG GCCCGCGAGA CCAGCGGGAC AGTCCGCGCC
    NotI

151 GCGGGAGACC AACTGGGACG AGCCGCGACC CACGCAGGCG CGCTGAGGCC

MTF-1      MTF-1                  A MTF-1
201 GGGGCAGGGG CgggcccGGC tggcgcgGCC GGCCTGCGGT TGgggcctg tsp1
            C  HNF-3      Sp1       Sp1    C       tsp2
251 gcgGGGGTGG GACgggccaA GCCgggcagG GCcgggatgg gGCCGCTGgc Myb           tsp3       AP-4, MED-1  A
301 gcttCCGTTG CTTGGATCAG TCTAGGTgca gctgccgGAT CC|TTCAGCGT
                                              BamHI +79

351 CTGCATCTCG GCGTCGCCCC GCGTACCGTC GCCCGGCTCT CCGCCGCTCT

401 CCCGGGGGTT CGGGGCACTT GGGTCCCACA GTCTGGGTGA GTGGTCGCAG

451 CCCGGGGAGG GGGCTCCTTC TGGAGAGGAG AGCGTGGTCG CGGGGC
```

CARRIER STATUS OF ANNEXIN A5 M2 HAPLOTYPE AND OBSTETRIC RISKS

CROSS-REFERENCE TO RELATED APPLICATIONS

This application is a § 371 National Stage Application of PCT/GB2015/051066, filed Apr. 7, 2015, which claims priority to U.S. Application No. 61/976,223, filed Apr. 7, 2014, U.S. Application No. 62/032,099, filed Aug. 1, 2014, U.S. Application No. 62/085,672, filed Dec. 1, 2014 and U.S. Application No. 62/115,230, filed Feb. 12, 2015. All of these documents (PCT/GB2015/051066, U.S. 61/976,223, 62/032,099, 62/085,672 and 62/115,230) are hereby incorporated by reference in their entirety.

FIELD OF THE INVENTION

The present invention relates to determining the carrier status of Annexin A5 M2 haplotype of parents (both male and female) prior to or after pregnancy to minimize the risk of pregnancy complications, including, but not limited to, recurrent pregnancy loss (RPL), infertility (such as, for example, unexplained male infertility, unexplained female infertility, infertility of unknown origin) in vitro fertilization (IVF) failure, intrauterine insemination (IUI) failure, foetal growth restriction (FGR), small for gestational age (SGA) newborn, intra-uterine foetal death (IUFD), gestational hypertension (GH), pre-eclampsia (PE) and/or venous thromboembolism (VTE). Once M2 carrier status is determined, methods of intervention, including administration of low molecular weight heparin (LMWH) and/or other anticoagulants can be administered either prior to and/or after pregnancy. Further methods of increasing rates of live births and/or IVF implantation and/or decreasing clinical miscarriage are also contemplated. Methods of detecting the carrier status as well as method of diagnosing and or predicting prognosis based on the M2 carrier status of a patient and/or couple is also contemplated.

BACKGROUND OF THE INVENTION

Thrombophilias are a major cause of adverse pregnancy outcome (Markoff et al, 2011) and there is increasing evidence to suggest that impairment of placental vasculature increases the risk of recurrent pregnancy loss (RPL), intra-uterine foetal death (IUFD), gestational hypertension (GH), pre-eclampsia (PE), venous thromboembolism (VTE), foetal growth restriction (FGR) and small-for gestational-age (SGA) newborns (Yotmis et al, 2003; Grandone et al, 2003; Chinni et al, 2009; Tisda et al, 2009; Grandone et al, 2010; Tiscia et al, 2012).

Normal pregnancy is an acquired hypercoagulable state and therefore women with a genetic predisposition to thrombophilia may develop clinical signs of coagulation defects de novo during pregnancy or during the postpartum period (Rey et al, 2003; Chunilal et al, 2009). The predisposing role of hereditary thrombophilic factors has been reported in several clinical studies (Rodger et al, 2010), and historically in the majority of patients the hereditary factor has been Factor V Leiden (FVL) or Prothrombin (PTm) (Bick et al, 2000). However, in 2007 a new hereditary factor for RPL and additional thrombophilia-related obstetric complications was identified (Bogdanova et al, 2007; Chinni et al, 2010). This defect, termed the M2 haplotype, is a sequence variation in the core promoter of the annexin A5 ANXA5 gene. It consists of four consecutive nucleotide substitutions in the core promoter and results in reduced expression of ANXA5 in placentas from M2 haplotype carriers when compared to non-carriers.

Annexin A5 is a member of the annexin protein family which share the properties of binding calcium and phospholipids. It is distributed abundantly and ubiquitously, mostly in kidney, liver and placenta (Morgan et al, 1998). It is most abundant on the apical membranes of placental syncytiotrophoblasts, the interface between maternal and foetal circulation. ANXA5 was originally named "placental anticoagulant protein". It has been extensively studied both in-vivo and in-vitro (Thiagarajan et al, 1990; Romisch et al, 1991). It has potent anticoagulant properties associated with the phospholipid-binding activity and is one of the few annexins to be found extracellularly (Gerke et al, 2005). The ability of ANXA5 to form two-dimensional aggregates on cell membranes has led to the development of the ANXA5 "protective shield" model that postulates that ANXA5 shields phospholipids at this site from availability for coagulation reactions and thus contributes to the maintenance of blood fluidity in the placenta.

Annexin 5 is deficient in placentas of patients with antiphospholipid syndrome (APS), and antiphospholipid antibody-mediated reduction of Annexin 5 on vascular endothelium may also contribute to systemic thrombosis (Rand, 1999). Bogdanova et al (2012) revisited the annexin A5 protective shield model and reported that preliminary genotyping analysis of a cohort of 30 lupus anticoagulant patients (LAC-positive) with obstetric APS revealed that 11 out of 30 were M2 carriers and suggesting a threefold relative risk to develop obstetric antiphospholipid antibodies (aPA).

In very preliminary data in examining placental tissue, Markoff et al (2010) suggested not only that the decreased ANXA5 expression in M2/ANXA5 placentas (including those from women with FGR and or PE) is the result of carriage of the M2 haplotype, but that this may occur regardless of parental origin, with obvious consequences for embryonal induced risk rather than wholly maternal. They observed that the normal ANXA5 allele does not compensate for observed M2 allele-specific decreased messenger RNA levels and suggested that unlike FVL and PTm, where paternal thrombophilic genes are not associated with RPL (Toth et al, 2008), the M2/ANXA5 acts via the embryo.

This led to a pilot study of 30 RPL couples where all other causes of RPL had been excluded (including inherited thrombophilias and APS). In this small and not powered sampling, the study suggested that male and females in these RPL couples may have an equal and increased M2 carriership when compared to control populations. The authors concluded that paternal and maternal carriage of the M2/ANXA5 haplotype may associate with RPL and confer equal risks. They further hypothesized that M2/ANXA5 may be the first instance of a hereditary factor causing pregnancy pathology by affecting embryonic anticoagulation (Rogenhofer et al, 2012).

Ueki et al 2012 in their knockout murine model found significant reductions both in litter size and foetal weight in ANXA5-null mice (ANXA5-KO) and thus demonstrated that the maternal supply of ANXA5 to the circulation was crucial for maintaining normal pregnancy. They further observed that cross-breeding of ANXA5-KO and WT mice showed only litters bred using ANXA5-KO females had reduced numbers of pups. They also demonstrated that administration of heparin on pregnancy days 12, 14 and 16 to ANXA5-KO mice significantly increased litter size.

However, when these animal studies were extended to humans, the use of low molecular weight heparin showed no beneficial effect. For example, in Rodger et al. reported in the journal Lancet that "previously published high-quality evidence" existed suggesting "no benefit of antepartum low-molecule-weight heparin in women with previous pregnancy loss, women with previous non-severe or late-onset pre-eclampsia, or women with previous small-for-gestational-age birth between the 5th and 10th percentile." See, Rodger et al., "*Antepartum Dalteparin Versus No Antepartum Dalteparin For the Prevention Of Pregnancy Complications In Pregnant Women With Thrombophilia (TIPPS): A Multinational Open-Label Randomised Trial*," Lancet 2014 Nov. 8; 384(9955):1673-83. Therefore, the authors designed an adequately powered study (that took 12 years to perform) to finally answer with statistical evidence this open question. Specifically, Rodgers et al. explained Our randomised trial is the first to show that thrombophilic women without previous venous thrombosis do not benefit from antepartum low-molecular-weight-heparin. Our meta-analysis shows that lower quality evidence suggests that low-molecular-weight heparin might prevent recurrent severe placenta-mediated pregnancy complications (severe or early-onset pre-eclampsia, small-for-gestational-age birth <5th percentile, and placental abruption) but we did not record this benefit in the subgroup analyses of our trial.

Rodger et al., page 9.

The authors further stated:

This trial addresses a key therapeutic question in a large and vulnerable patient group. The absence of benefit is an important finding. The discovery of an association between thrombophilia and pregnancy complications in the mid-1990s led to widespread off-label use of low-molecular-weight heparin in pregnant women-both with and without thrombophilia-who had previous pregnancy complications. This off-label use has been fuelled by the emotional consequences of these complications combined with expert opinion, consensus panels and small non-randomised studies suggesting benefit. Antepartum low-molecular-weight heparin is not a benign intervention; it can be complicated by heparin-induced thrombocytopenia (albeit rarely), withholding of epidural analgesia, and, as shown in our trial, increased minor bleeding, allergic reactions, skin reactions, raised liver transaminase concentrations, and the risk of induction of labour. Additionally, up to 400 subcutaneous injections of the drug per term of pregnancy is both a personal and financial burden. Clinicians and patients can be reassured that dalteparin use throughout the antepartum period does not lead to significant changes in bone mineral density. Finally, the continued belief in ineffective therapy hampers further research for efficacious treatments for women at risk of venous thromboembolism and pregnancy complications.

Rodger, page 8.

Thus, there is a need for improved methods of reducing pregnancy complications associated with thrombophilia caused by ANXA5 M2 haplotype.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject.

The present invention relates to a method of treating an M2 haplotype pregnancy, wherein a M2 haplotype pregnancy is identified when it is determined that either the biological mother or the biological father is a carrier of the ANXA5 M2 haplotype and then the mother of a M2 haplotype pregnancy is administered an effective amount of an anticoagulant. Surprisingly and contrary to the results obtained in other clinical trials, if the anticoagulant is administered immediately prior to, at the same time, and/or immediately after conception, intrauterine insemination, embryo transfer and/or implantation, the rate of live births are substantially improved. In some embodiments, both the biological mother and the biological father are found to be carriers of the A5 M2 haplotype.

Other embodiments of the invention include a method of reducing obstetric complications comprising identifying a M2 haplotype pregnancy, wherein said M2 haplotype pregnancy exists when either the biological mother or the biological father is a carrier of the ANXA5 M2 haplotype and then administering to the mother of a M2 haplotype pregnancy an effective amount of an anticoagulant, wherein said anticoagulant reduces the risk of obstetric complications. Preferably, the anticoagulant is administered immediately prior to, at the same time and/or immediately after conception, intrauterine insemination, embryo transfer and/or implantation. In other embodiments, the anticoagulant is administered for at least 4 weeks, for at least 8 weeks, for at least 12 weeks, or for at least 16 weeks. Examples of obstetric complications include, but are not limited to: recurrent pregnancy loss (RPL), infertility, in vitro fertilization (IVF) failure, intrauterine insemination (IUI) failure, foetal growth restriction (FGR), small for gestational age (SGA) newborn, intra-uterine foetal death (IUFD), gestational hypertension (GH), pre-eclampsia (PE) and/or venous thromboembolism (VTE).

Other preferred embodiments of the invention include a method of determining a M2 haplotype pregnancy, comprising identifying the M2 haplotype carrier status either the biological mother or the biological father, wherein said identification is determined based on genomic analysis; recording the M2 haplotype carrier status of the biological mother and the biological father; reporting whether a M2 haplotype pregnancy exists if either the biological mother or the biological father is a carrier of the ANXA5 M2 haplotype. Preferred methods of detection include sequencing, PCR and/or SNP detection techniques.

Once M2 carrier status is determined, methods of intervention, including administration of low molecular weight heparin (LMWH) and/or other anti-coagulants can be administered either prior to and/or after pregnancy. Preferably, the anticoagulant is administered immediately prior to, at the same time and/or immediately after conception, intrauterine insemination, embryo transfer and/or implantation. Thus, further methods of increasing rates of live births and/or IVF implantation and/or clinical pregnancy and/or decreasing clinical miscarriage are contemplated. In other embodiments, the anticoagulant increases the rate of implantation. In other embodiments, the anticoagulant decreases the rate of miscarriage prior to detection of a foetal heartbeat. For example, in preferred embodiments, the mother of an ANXA5 M2 haplotype pregnancy is administered an anticoagulant immediately after detecting pregnancy using methods to detect early pregnancy as soon as it is established. In other embodiments, the anticoagulant is administered at the same time of embryo transfer in an IVF setting.

In even further preferred embodiments, the anticoagulant is administered prior to pregnancy or embryo transfer in an IVF setting. In other embodiments, the anticoagulant is administered until the mother delivers the baby.

In other preferred embodiments, the anticoagulant is low-molecular weight heparin ("LMWH"). In preferred embodiments, the anticoagulant is administered as part of in vitro fertilization. The mother may be administered LMWH at the time of embryo transfer, prior to embryo transfer or within days of embryo transfer during IVF treatment. Preferably, administration of an anticoagulant, such as LMWH, occurs simultaneously with embryo transfer. In other embodiments, the LMWH is administered for at least 4 weeks, for at least 8 weeks, for at least 12 weeks, or for at least 16 weeks. In other embodiments, the LMWH is administered until the mother delivers the baby.

BRIEF DESCRIPTION OF DRAWINGS

FIG. 1 depicts an ANXA5 promoter structure as disclosed in Carcedo (2001), Biochem. J. 356, 571-579) and Bogdanova N, Horst J, Chlystun M, Croucher P J, Nebel A, Bohring A, Todorova A, Schreiber S, Gerke V, Krawczak M, Markoff A (SEQ ID NO: 1). A common haplotype of the annexin (ANXA5) gene promoter is associated with recurrent pregnancy loss. Hum Mol Genet 2007; 16: 573-78. As reported in Bogdanova, FIG. 1 shows the structure of the ANXA5 gene core promoter region. The boundaries are marked by vertical bars and are numbered according to the position of the first transcription start point (tspl). Non-translated exon 1 is shaded in gray. Transcription factor consensus motifs are in small print, and abbreviations of the corresponding transcription factors are displayed in italics above the sequence information. NotI and BamHI restriction sites are underlined and the sequence of the Z-DNA stretch in the promoter is given in italics. Nucleotides marking transcription start points (tsp) are underlined. Regions important for promoter function (motifs A and B) cover nucleotide positions 295-311 and 328-337. Nucleotides changed in the M2 ANXA5 promoter haplotype are printed in bold and substituting nucleotides are given in bold capital letters on top of the respective positions. In Bogdanova et al., the position of M2 ANXA5 haplotype substitutions are designated as −19G→A, 1A→C, 27T→C and 76G→A (see, for example, page 574, first paragraph under "Results") and correspond to 243G→A, 262A→C, 288T→C and 337G→A as shown in FIG. 1 herein. Similarly, these same substitutions also have been referred to as: (1) G to A at a position which corresponds to nucleotide 186 of SEQ ID No. 2 in US2012/0178156; (2) A to C at a position which corresponds to nucleotide 203 of SEQ ID No. 2 in US2012/0178156; (3) T to C at a position which corresponds to nucleotide 229 of SEQ ID No. 2 in US2012/0178156; and (4) G to A at a position which corresponds to nucleotide 276 of SEQ ID No. 2 in US2012/0178156.

DETAILED DESCRIPTION

The details of one or more embodiments of the invention are set forth in the description below. Other features, objects, and advantages of the invention will be apparent from the description and drawings, and from the claims.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to a "polynucleotide" includes a mixture of two or more such polynucleotide molecules or a plurality of such polynucleotide molecules.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

The invention will be described in more detail below.

A. Definitions

In the present invention, a "M2 haplotype pregnancy," or an "ANXA5 M2 haplotype pregnancy" is defined as a pregnancy where either the biological mother and/or the biological father are carrier(s) for the annexin ANXA5 M2 haplotype. It is contemplated that a "M2 haplotype pregnancy" includes situations where the biological mother has yet to become pregnant. Moreover, in the situation of a surrogate mother, both donor egg and/or sperm should be screened as well as the recipient mother for her own risk.

In the present invention, "annexin A5 M2 haplotype," "M2 haplotype," or "ANXA5 M2 haplotype" (SEQ ID NO: 2) is defined as a substitution in the annexin (ANXA5) promoter, wherein the substitutions are:
  (i) a point mutation G to A at a position which corresponds to nucleotide 243 of FIG. 1;
  (ii) a point mutation A to C at a position which corresponds to nucleotide 262 of FIG. 1;
  (iii) a point mutation T to C at a position which corresponds to nucleotide 288 of FIG. 1; and
  (iv) a point mutation G to A at a position which corresponds to nucleotide 337 of FIG. 1.

In the present invention, "M1 haplotype," "annexin A5 M1 haplotype," or "ANXA5 M1 haplotype" (SEQ ID NO: 3) is also disclosed in WO 2006/053725 and Bogdanova et al., and is characterized by the following two nucleotide exchanges (1) A to C at a position which corresponds to nucleotide 262 of FIG. 1, and (2) T to C at a position which corresponds to nucleotide 288 of FIG. 1.

In the present invention, an "anticoagulant" is defined as a drug used to prevent dot formation or to prevent a clot that has formed from enlarging. Anticoagulant drugs inhibit dot formation by blocking the action of dotting factors or platelets. Anticoagulant drugs fall into three groups: inhibitors of clotting factor synthesis, inhibitors of thrombin and antiplatelet drugs. Anticoagulants may be administered at the time (e.g., simultaneously with and/or during the same procedure) of embryo transfer or IUI, for example, or shortly (for example, within 1 day, within 2 days, within 3 days, within 4 days, within 5 days, within 6 days, within 7 days, within 8 days, within 9 days, within 10 days, within 11 days, within 12 days, within 13 days, or within 14 days) after conception, implantation, IUI, embryo transfer, becoming pregnant and/or of learning of the pregnancy. Anticoagulants may be administered for at least 4 weeks, for at least 8 weeks, for at least 12 weeks, or for at least 16 weeks. Anti coagulants may be administered until the mother delivers the baby. Additionally, an anticoagulant may be administered immediately before (for example, within 1 day, within 2 days, within 3 days, within 4 days, within 5 days, within 6 days, within 7 days, within 8 days, within 9 days, within 10 days, within 11 days, within 12 days, within 13 days, or within 14 days) prior to becoming pregnant, conception, implantation, IUI and/or embryo transfer.

Preferred examples of anticoagulants include, but are not limited low molecular weight heparin (LMWH) or aspirin, and preferably low dose aspirin.

In specific preferred embodiments, Low Molecular Weight Heparin (LMWH) is administered to the pregnant mother. LMWH can be purchased by a number of different commercial sources. In the present invention, LMWH is may be administered to a patient every day throughout pregnancy until shortly before delivery based on the treating physician's judgment. Female carriers of the M2 haplotype should also receive LMWH following delivery and for 6 weeks thereafter to reduce the risk of venous thromboembolism (VTE). LMWH may be administered at the time (e.g., simultaneously with and/or during the same procedure) of embryo transfer or IUI, for example, or shortly (for example, within 1 day, within 2 days, within 3 days, within 4 days, within 5 days, within 6 days, within 7 days, within 8 days, within 9 days, within 10 days, within 11 days, within 12 days, within 13 days, or within 14 days) after conception, implantation, IUI, embryo transfer, becoming pregnant and/or learning of pregnancy. LMWH may be administered for at least 4 weeks, for at least 8 weeks, for at least 12 weeks, or for at least 16 weeks. LMWH may be administered until the mother delivers the baby. Additionally, LMWH may be administered immediately before (for example, within 1 day, within 2 days, within 3 days, within 4 days, within 5 days, within 6 days, within 7 days, within 8 days, within 9 days, within 10 days, within 11 days, within 12 days, within 13 days, or within 14 days) prior to becoming pregnant, conception, implantation, IUI and/or embryo transfer.

As used herein, the phrase "at the same time" is defined as within hours of undergoing fertilization, IUI, conception and/or embryo transfer. Preferably, "within hours" is defined as within 30 mins, 1, 2, 3, 4, 5, 6, 7, 8 9, or 10 hours of undergoing fertilization, IUI, conception and/or embryo transfer.

As used herein, "intrauterine insemination" or "IUI" refers to a type of artificial insemination where a concentrated solution of sperm is placed directly in the uterus or vagina around the time of egg release from the ovaries. IUI may be performed with or without hormones and/or other drugs (e.g., such as Clomid) to increase the number of released eggs from the ovaries.

In the present invention, "obstetric complications" are defined as complications arising during pregnancy due to thrombophilia and/or impaired placental vasculature. Examples of obstetrics complications, include, but are not limited to: recurrent pregnancy loss (RPL), infertility, in vitro fertilization (IVF) failure, IUI failure, foetal growth restriction (FGR), small for gestational age (SGA) newborn, intra-uterine foetal death (IUFD), still birth, gestational hypertension (GH), pre-eclampsia (PE) and/or venous thromboembolism (VTE).

In the present invention, the anticoagulant is effective to increase the rate of implantation. In other embodiments, the anticoagulant is effective to decrease the rate of early miscarriage (i.e. prior to the detection of a foetal heartbeat).

In the present invention, "infertility" is defined as the inability for a couple to become pregnant, even when attempting pregnancy by monitoring ovulation and/or by being administered hormones and/or other drug (e.g., Clomid) to increase the chance of pregnancy. Examples of infertility include, and are not limited to unexplained male infertility, unexplained female infertility, and/or infertility of unknown origin.

It will be understood that in the context of the embodiments described herein, the female subject was made pregnant by the herein mentioned "biological father". Thus, as used herein, the term "biological father" means the biological father of the human embryo of the herein defined female subject. In some embodiments, the female subject is already pregnant and is therefore the "biological mother" in other embodiments the female subject is not yet pregnant and is therefore the intended "biological mother."

The term "intended biological father" therefore means that the female subject is not yet made pregnant by the human male subject, but that it is intended that the human female subject will be made pregnant by said human male subject. During that time, also the female subject is the "intended" biological mother. Once the female subject was made pregnant by said human male subject, the "intended biological father" becomes the "biological father" and the "intended biological mother" becomes the "biological mother".

The methods of the present invention therefore encompass situations wherein the female subject is not yet made pregnant by the intended biological father, i.e. the female and/or the intended biological mother and the intended biological father plan to test the predisposition of the female subject to obstetric complications prior to the pregnancy. This includes for example couples which plan to have a baby or females which plan to become pregnant, either by natural procreation or by in vitro fertilization.

The methods of the present invention can be used to increase the rates of live births, to increase the incidence of implantation, increase the incidence of clinical pregnancy, and/or decrease the rates of clinical miscarriage. In the present invention, the phrase "live births" is defined as a successful delivery of a living baby regardless of whether the baby is full term.

"Clinical miscarriage" is defined as whether the fertilized embryo (for example, during in vitro fertilization the embryo transfer) results in a clinical miscarriage or a live birth. Patients reach a "clinical pregnancy" stage when pregnancy can be confirmed, such as by an ultrasound scan detecting a foetal heart(s)

The present invention "implantation" refers to the ability (even if temporary) of an embryo to adhere to the uterine wall.

The methods of the present invention further encompass situations wherein the female subject is already pregnant. In such cases, it might still be wanted to test the predisposition of the female subject to obstetric complications, either by way of testing a sample of the biological father and/or by way of testing an embryonic sample of the embryo as such (for example by circulating foetal cells, by way of chorion biopsy or by way of amniocentesis, both resulting in samples of embryonic origin). Additionally, but not exclusively, it is also envisaged to test the (intended) biological mother.

Provided that the fertilization is conducted in vitro, i.e. by way of an in vitro fertilization, it is also envisaged to analyse a single cell sample obtained before or during the morula stage of the in vitro fertilized embryo, prior to its implantation into said female subject.

The "morula stage" denotes the 16 cell stage of human embryogenesis. "Before or during the morula stage" means that it is also envisaged to obtain one single cell prior to the 16-cell stadium, for example during the 6-8 cell stadium of human embryogenesis.

In vitro fertilisation (IVF) is a well-known process by which egg cells are fertilised by sperm outside the womb, in vitro.

It is also envisaged that females which intend to become pregnant by a sperm donor, make use of the methods of the present invention in order to test their predisposition to obstetric complications by way of testing the respective sperm donor sample before it is used for the in vitro fertilization of the respective female subject and then being treated with an anticoagulant prior to, at the same time and/or immediately after conception, intrauterine insemination, embryo transfer and/or implantation. The present invention and in particular the methods of the present invention therefore also encompass a stratification method for selecting a sperm donor, which is not a carrier of the risk haplotype M2.

Thus, by way of the methods of the present invention it is possible to detect and subsequently select a sperm donor who, in all likelihood, will not contribute to the predisposition of the respective female subject to obstetric complications. These stratification methods make particularly sense when a maternal sample of the mother was already tested to be no carrier of the risk haplotype M2, because in such cases it is of importance to test whether the intended biological father (for example the sperm donor) is a carrier of the mentioned risk haplotypes. If so, then it might be reasonable to select a different sperm donor, preferably sperm donor who is also no carrier of the risk haplotypes M2.

In the same way, it is reasonable and therefore particularly envisaged in the embodiments of the present invention to test the intended biological father or the biological father in situation where the biological mother (or the intended biological mother) is no carrier of the risk haplotype M2 (as tested in a maternal sample).

It is also envisaged that females which intend to become pregnant by a donor eggs, make use of the methods of the present invention in order to test their predisposition to obstetric complications by way of testing the respective egg donor genotype before it is used for the in vitro fertilization. The present invention and in particular the methods of the present invention therefore also encompass a stratification method for selecting an egg donor, which is not a carrier of the risk haplotype M2.

Thus, by way of the methods of the present invention it is possible to detect and subsequently select egg donors who, in all likelihood, will not contribute to the predisposition of the respective female subject to obstetric complications. These stratification methods make particularly sense when a maternal sample of the mother was already tested to be not a carrier of the risk haplotype M2, because in such cases it is of importance to test whether the intended biological egg donor is a carrier of the mentioned risk haplotypes. If so, then it might be reasonable to select a different egg donor, preferably an egg donor who is also no carrier of the risk haplotypes M2.

In the same way, it is reasonable and therefore particularly envisaged in the embodiments of the present invention to test the intended biological egg donor and/or the biological father in situation where the mother (or the intended mother) is no carrier of the risk haplotype M2 (as tested in a maternal sample).

In the present invention, both the mother but also the father can contribute to a predisposition of the female subject to obstetric complications. Accordingly, even if the female subject as such is not a carrier of the risk haplotype (tested in a maternal sample), the biological father and/or the intended biological father can still contribute to the above mentioned predisposition and should, therefore, be tested as well.

Provided that either the biological father of the embryo or the biological mother of the embryo is a heterozygous carrier of the risk haplotype, it is also possible to test a sample of said embryo (e.g. a chorion biopsy sample or a single cell sample described herein) in order to test whether it is carrier of the risk haplotype or not (for example in case of an in vitro fertilization). Provided that either the biological mother or the biological father is a homozygous carrier of the risk haplotype, it appears unnecessary to test the embryo as well, as the heterozygous presence of the risk haplotypes M2 is already indicative for a predisposition of the respective female subject to obstetric complications. Provided that the biological father is untraceable or unknown, and further that the female subject (in that case the biological mother) is not a carrier of the M2 risk haplotype, one might still want to test the predisposition of the respective female subject to obstetric complications. In that case it is envisaged to test a sample which originates from the embryo (e.g. circulating foetal blood cells, chorion biopsy and/or amniocentesis sample). It will be understood, however, that an embryonic sample should preferably not be obtained solely because the female subject intends to test its predisposition to obstetric complications. It is rather envisaged to test in samples which originate from the embryo only then, when such samples are already at hand for other reasons.

In the present invention, recurrent pregnancy loss (RPL) is typically characterized as the occurrence of two or more pregnancies that end in miscarriage of the foetus. Said two or more pregnancies occur either consecutively or intermittently, consecutively being preferred.

In the present invention, pre-eclampsia (PE) is a medical condition in which hypertension arises in pregnancy (pregnancy-induced hypertension).

Foetal growth restriction (or foetal growth retardation) is a condition in which a foetus does not grow appropriately. FGR should be suspected for example when the fundal height is more than 3 cm less than predicted.

It is envisaged that in the methods of the present invention, said sample obtained from the individual (whether mother or father) from a blood sample, a sperm sample, a tissue sample, or a cell sample. It will be understood that any biological sample will be suitable as long as the respective sample contains genetic material which allows the detection/diagnosis which are subject of the methods of the present invention.

Such a sample may be obtained via biopsy such as needle biopsy, surgical biopsy, via any kind of smear technique, for example by use of a buccal swab, etc. or others. The skilled person is well aware of further means and methods enabling him or her to obtain a sample containing genetic material from a human subject.

The skilled person is well-aware how to avoid or circumvent such contaminations "the corresponding standards are for example summarized in the "General standards and guidelines for prenatal testing are available from the American College of Medical Genetics (2006 Edition of Standards and guidelines for clinical genetics laboratories, http://www.acmg.net/Pages/ACMG_Activities/stds-2002/g.htm".

B. Methods of Detecting

As already disclosed in WO 2006/053725 and Bogdanova N, Horst J, Chlystun M, Croucher P J, Nebel A, Bohring A, Todorova A, Schreiber S, Gerke V, Krawczak M, Markoff A. A common haplotype of the annexin (ANXA5) gene promoter is associated with recurrent pregnancy loss. In Hum Mol Genet 2007; 16: 573-78, the risk haplotype M2 which can be detected in the human ANXA5 promoter, is characterized by the following four nucleotide exchanges:

(1) G to A at a position which corresponds to nucleotide 243 of FIG. 1;
(2) A to C at a position which corresponds to nucleotide 262 of FIG. 1;
(3) T to C at a position which corresponds to nucleotide 288 of FIG. 1; and
(4) G to A at a position which corresponds to nucleotide 337 of FIG. 1 (SEQ ID NO: 2).

The risk haplotype M1 which can also be detected in the human ANXA5 promoter, is also disclosed in WO 2006/053725 and Bogdanova et al., and is characterized by the following two nucleotide exchanges (1) A to C at a position which corresponds to nucleotide 262 of FIG. 1, and (2) T to C at a position which corresponds to nucleotide 288 of FIG. 1 (SEQ ID NO: 3). FIG. 1 depicts an ANXA5 promoter structure as disclosed in Carcedo (2001), Biochem. J. 356, 571-579) and Bogdanova et al (SEQ ID NO: 1).

Means and methods to determine and/or to detect the M2 haplotypes are well-known (see for example WO 2006/053725 and Bogdanova et al.) and additionally disclosed in detail herein.

"Nucleic acid detection techniques" are well-known to the skilled person and include inter alia any kind of PCR-based techniques or any other suitable technique which allows the identification of the nucleotide exchanges which characterize the risk haplotype M2. Such methods are described herein (see the examples) and are also published for example in WO 2006/053725.

Said techniques may be selected from the non-limiting group consisting of hybridization techniques, nucleic acid sequencing, PCR, restriction fragment determination, single nucleotide polymorphism (SNPs)-determination, LCR (ligation chain reaction) or restriction fragment length polymorphism (RFLP)-determination, to name some.

Corresponding examples and further details may be obtained from standard technical advice literature (like Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.)). As documented in the examples of WO 2006/053725, a further suitable method is the restriction fragment determination or the RFLP method, comprising the determination of a BamHI restriction site. As shown in WO 2006/053725, the absence (BamHI') or the presence (BamHI+) of a BamHI restriction site is determined, and is indicative for the absence or presence of a point mutation as defined herein. Details on this method are given in the appended examples of WO 2006/053725.

In one embodiment, a relevant DNA-stretch may be amplified from genomic DNA by PCR-technology. Potential primers to be employed comprise, but are not limited to, the primers as provided in SEQ ID NO: 4 (ANX5.P.F; SEQ ID NO: 22 of WO 2006/053725) and SEQ ID NO: 5 (ANX5.exl.R; SEQ ID NO: 23 of WO 2006/053725). The person skilled in the art is readily in the position to deduce further primer pairs or primers to be employed in order to amplify relevant stretches of the herein defined annexin A5 (ANXA5) promoter or of its fragments. After the amplicon is obtained (see also experimental part) it can be digested (restriction digest) with the restriction enzyme BamHI (which can be obtained from various suppliers, inter alia: Roche Applied Science, Mannheim, Germany; MBI Fermentas, St. Leon-Rot, Germany; New England Biolabs, Frankfurt am Main, Germany. Again, details are given in the experimental part. After this digest, to be carried in accordance with methods well-known in the art (see inter alia Sambrook/Russel, 2001, (log.cit.)), further analysis of the BamHI/BamHI+restriction site can be carried out by known techniques, like gel analysis, e.g. agarose gel analysis.

A further technique which is particularly envisaged in the context of the present invention is the SNP detection technique established by IHG Pharmaco. Said technique is sufficiently explained in WO 2006/038037 and in U.S. Pat. No. 7,803,545 and is hereby incorporated by reference in its entirety.

Specifically, in genotyping using IHG technology, a sample of nucleic acid is obtained from the subject, and the gene segment containing the polymorphic site is amplified to provide a population of amplicons bearing the sequence of the gene segment. Typically, this amplification of the gene segment is accomplished by PCR using a pair of primers which flank the said gene segment. Suitable primers are selected which are specific for the gene segment under consideration. Primers are selected to amplify a gene segment which is of the order of from 90 to 400 bases in length, and preferably of the order of 100 to 150 base pairs in length. It is normally preferred that the polymorphic site is located in the central region of the gene segment, that is to say approximately in the central third of the gene segment. PCR amplification of the gene segment will result in a population of double stranded amplicons, as is well known. More details of the procedure which may be used for PCR amplification can be found in WO 93/19201.

Where the nucleic acid under examination is mammalian genomic DNA, a sample of the DNA is obtained from an individual or other object whose genotype for a specific characteristic it is wished to study. (The term "individual" is intended to include a foetus.) DNA can be extracted from all nucleated cells. Typically, the DNA is obtained from peripheral blood cells for convenience. Foetal DNA can be obtained from placental cells or amniotic fluid. Other sources of DNA include hair follicles, mummified bodies, etc. The DNA may be isolated by any appropriate method, for example by the rapid salting out method described by Miller et al (Miller, S., Dykes, D. and Polesky, H. (1988) "A simple salting out procedure for extracting DNA from human nucleated cells"; Nucl. Acids Res. 16:1215). Alternatively, the DNA may be isolated as cDNA from mRNA by reverse transcription.

A population of an IHG molecule which has a sequence corresponding to the gene segment, but modified as discussed herein to include controlled nucleotide substitution, deletion, insertion or combination thereof is also provided. Typically, the IHG population is prepared by amplification using, for example PCR. Again, more details of the procedure which may be used for PCR amplification can be found in WO 93/19201, which is hereby incorporated by reference in its entirety. The primers chosen for the PCR are selected to provide amplification of the IHG molecule. PCR amplification will result in a population of double stranded IHG amplicons. The IHG may preferably be substantially identical in length to the gene segment under consideration (disregarding any necessary inserted or deleted bases of the IHG), or may be a different length, for example shorter than or longer than the gene segment. However, if the gene segment and IHG are of different length (disregarding any necessary inserted or deleted bases of the IHG), there must be a sufficient degree of overlap to permit heteroduplex formation between the amplified populations of the gene segment and the IHG. The primers used in amplifying the IHG and the gene segment respectively may be the same or different. Typically, however, the same primers are used, resulting in amplified IHG and gene segment which are of substantially the same length (disregarding any necessary inserted or deleted bases in the IHG). As taught in WO 93/19201, the primers may be labelled.

PCR amplification of the gene segment and the IHG may be accomplished in the same or separate vessels ("mixed" or "separate" PCR respectively). It is preferred to conduct amplification separately and then to combine or pool the amplified populations of the gene segment and the IHG in order to permit heteroduplex formation to proceed.

Heteroduplex formation between the combined populations of IHG and the gene segment which contains the polymorphic site is accomplished by first heating the combined population of IHG and gene segment in order to separate the double stranded DNA into single stranded DNA and then cooling to permit heteroduplex formation, as described for example in WO-A-93/19201.

The heteroduplexes formed are separated according to their molecular conformation which affects their apparent, but not actual, molecular weight. This may be achieved by, for example, electrophoresis. The separation is typically effected on a gel which does not fully denature the nucleic acid, such as a non-denaturing polyacrylamide gel. Electrophoresis is conducted under conditions which effect a desired degree of resolution of the duplexes. A degree of resolution that separates duplexes that differ in "apparent size"—resulting from their different molecular conformations—by as little as about 10 bp is usually sufficient. Size markers may also be run on the gel to permit estimation of the mobility and thus the apparent size of duplexes. In addition, or alternatively, a control DNA molecule having a sequence which corresponds to the known allele of the gene under consideration can also be separately amplified using PCR and allowed to form heteroduplexes with the IHG being used, with the resultant sample then being run on the gel to provide markers on the gel for the different heteroduplexes which result.

The distribution, i.e. the resolution pattern, of the heteroduplexes will be allele-specific. This resolution pattern or PCR fingerprint can next be visualised. Where the PCR primers have been labelled, this label may be revealed. A substrate carrying the separated labelled duplexes is contacted with a reagent which detects the presence of the label. Where the PCR primers were not labelled, the substrate bearing the PCR fingerprint may be contacted with, for example, ethidium bromide or SYBR™ green (available from Molecular Probes) and the nucleic acid fragments visualised under ultraviolet light; alternatively, the heteroduplexes may be visualised with silver staining.

Additional methods of detecting M2 haplotype status, include, but are not limited to methods utilizing a fluorescent molecule and/or a solid phase. Preferred solid phase structures can be beads and/or plates. Solid phases can comprise plastic, silicon, glass, polystyrene, aluminium, steel, iron, copper, nickel, silver, gold, nitrocellulose or nylon. Additionally, oligos at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29 and/or at least 30 nucleotides in length can be used to detect the ANXA5 M2 haplotype. Moreover, methods of detecting ANXA5 M2 haplotype status can include methods utilizing Next Generation Sequencing techniques. These methods of detecting are all within the skill in the art.

EXAMPLES

Example 1

Study Population

Study patients were recruited between March 2012 and February 2013 from patients attending five fertility clinics.

Informed consent was obtained from all patients. During this period 314 patients (157 couples) presented with at least 1 previously failed IVF cycle (average 1.9 IVF and 0.2 IUI). A detailed clinical history was obtained and the genotyping for presence or absence of carriage of the M2/ANXA5 haplotype, formed part of the diagnostic investigations for infertility. The mean age of females was 36.3 years (Range 23 to 49) and that of their male partners 38.6 years (Range 23 to 64). Average Body Mass Index of the females was 25.5 (range, 19 to 40.5) and that of their male partners was 33.7 (Range 21 to 36). The selection of patients for screening was based on their prior history and the patient's willingness to be tested, following the detailed nature of the study being provided to them at consultation. Female patients were screened for antiphospholipid antibodies. With regard to their infertility status, the majority of the male population had oligospermia (48%), astheno/oligoasthenospermia (27%), or azoospermia (13%). These varied according to carrier status with an incidence in the non-carriers of 41%, 26% and 11%, respectively; and for the carriers 35%, 12%, and 12%, respectively. With regard to the female population, the most prevalent was unexplained (27%), poor ovarian reserve (17%), PCOS (11%), and endometriosis (6%). The variation according to carrier status with an incidence in the non-carriers was 30%, 16%, 16% and 3%, respectively; and for the carriers 26%, 9%, 18%, and 8%, respectively.

The majority of these patients were White British (77% males and 75% females), Indian/Pakistani (8%) the remainder being of diverse ethnicities. As a whole this cohort is representative of the demography of the UK and Eire.

Example 2

Collection of DNA and Determination of M2 Carrier Status

Deoxyribonucleic acid (DNA) was collected from couples either by a blood sample (the first cohort), with the remaining cohort undergoing buccal cell analysis on specific collection paper. Extensive laboratory tests were undertaken to ensure the transfer to buccal cell collection caused no deterioration in the quality of the data. DNA was extracted from white blood cells using QIAmp DNA blood mini kit (Qiagen GmbH, Hilden, Germany) or from elution off the collecting paper. PCR reactions were carried out on 100 ng of genomic DNA isolated from blood samples using the Qiamp blood mini kit or from purified collecting paper punches included in subsequent PCR reactions as template. PCR reactions were carried out using Biotaq Polymerase (Bioline. Bioline Reagents Limited, London, Great Britain) in a volume of 25 µl containing 10× $NH_4$ Reaction Buffer: 160 mM $(NH_4)_2SO_4$, 670 mM Tris-HCl (pH 8.8), 50 mM $MgCl_2$ (final concentration 1.5 mM), 50 pM primer (forward and reverse), 200 µM dNTP's, polymate additive (Bioline) and 2.5 units Biotaq polymerase. PCR cycling conditions were as follows, 94° C. for 45 seconds, 30 cycles of 94° C. for 30 seconds—60° C. for 30 seconds—68° C. for 1 minute and a final extension step of 7 minutes. PCR products were purified using standard column purification methods using a Zymo ZR-96DNA Clean and Concentrator kit (Zymo Research Corporation. Irvine, Calif., USA). Purified amplicons were sequenced using ABI BigDye terminator chemistry v3.1 using standard conditions and electrophoresed on an ABI 3730x1 DNA analyser. Traces were analysed and genotyped using ABI Seqscape v 2.5. (Applied Biosystems, Foster City, Calif., USA). The presence of the M2 haplotype (a set of four consecutive nucleotide substitutions in the ANXA5 gene promoter: 243G/A [rs112782763], 262A/C [rs28717001], 288T/C [rs28651243] and 337G/A [rs113588187]) was investigated (SEQ ID NO: 2). When only two of the four variants (262A/C, 288T/C) were present, the haplotype was defined as M1 (SEQ ID NO: 3).

All genotype calls were made using the Seqscape software (Applied Biosystems, Foster City, Calif., USA) with a 25% mixed base calling threshold. Seqscape was programmed to analyse nucleotide variations at 4 specific bases as described in the literature. Results were generated in the form of a mutations report detailing mutations across the region of interest. Report production was carried out by means of an in house LIMS system (Laboratory Information Management System), which was programmed to only allow certain combinations of mutation. Any sample which gave an unexpected result was flagged by the LIMS system and checked by an operator before repeating the test on a fresh sample.

Example 3

Genotyping and Statistical Analysis

Patients who were heterozygous or homozygous carriers of the M2/ANXA5 haplotype were recorded as affected hetero or homozygous carriers. Tests for deviations from Hardy-Weinberg were performed using the method of Guo and Thompson, 1992 (also used by Bogdanova et al 2007 and Rogenhofer et al 2012). We performed this test within the male and female groups considered separately and overall. We also tested excluding the individuals of non-UK ethnicity to see whether this affected the results.

To check whether the significant deviation from Hardy-Weinberg equilibrium (HWE) observed in the female subgroup could be attributed to chance we subsampled 155 individuals at random from the entire set (males and females combined) and estimated the p-value for deviation from HWE using the same method and recorded the p-value. We performed this procedure 1000 times, and of these only 3 p-values recorded were more extreme than those observed for the all-female group, thus suggesting that the deviation from HWE in females is real and not attributable to chance.

The controls used for comparison are those used by Rogenhofer et al 2012 from a population control sample drafted from the PopGen biobank at University Clinic Schleswig-Holstein Kiel (n=533). PopGen population controls were from Northwest Germany and were healthy subjects identified through official population registers (Krawczak et al 2006). The sample used in this study comprised approximately equal numbers of men and women distributed among three age groups (18-30, 30-50, and 50-80 years). The cohort of Muenster fertile controls were anonymised individuals from the Institute's registry (Rogenhofer, et al 2012), all with successful pregnancies and no documented history of recurrent pregnancy loss.

Example 4

Patient Genotype Frequencies

Of the 314 patients (6 patients were not genotyped because 4 males (2 azospermia, 1 oligospermia 1 aged 65); 2 females: 1 early menopause 1 menopause) and 157 couples the overall patient carriage rate was 25% (N=78) and of similar incidence in females (24% N=37) and males (27% N=41). However, of couples there was a high (44%; n=69) incidence of M2 carriage (defined as one or both partners being M2 carriers or homozygotes). None of these patients tested positive for antiphospholipid syndrome (APS). Amongst these carrier couples were small subsets of couples in which one partner was a non-carrier and one was homozygous (4% N=7), or both partners were carriers (4% N=6), or one partner was a carrier and one homozygous (2% N=3). There were 9 female homozygotes and one male. The genotype distribution of male and female patients is shown in Table 1.

TABLE 1

Genotype Distributions of Male/Female Partners

| Genotype | Male | % | Female | % |
|---|---|---|---|---|
| N | 153 | | 155 | |
| N/N | 88 | 58% | 97 | 63% |
| N/M1 | 24 | 16% | 21 | 14% |
| M1/M1 | 0 | 0% | 0 | 0% |
| N/M2 | 37 | 24% | 27 | 17% |
| M1/M2 | 3 | 2% | 1 | 1% |
| M2/M2 | 1 | 1% | 9 | 6% |
| Total genotypes | 306 | 100% | 310 | 100% |

The genotypes N M1 M2 refer to haplotypes in the ANZXA5 gene promoter:
N = normal/Wild type;
M1 comprises 262A→C and 288T→C (six heterozygotes);
M2 comprises 243G→A, 262A→C, 288T→C and 337G→A (16 heterozygotes).

The genotypes expected under HWE and observed genotype frequencies are presented in Table 2 for males and females respectively. There is no significant deviation from HWE in males, but there is significant deviation amongst females (p=0.005). Restricting the analyses to individuals of British or Irish ethnicity gave similar results (data not shown).

TABLE 2

Observed and HWE Expected Genotype Counts for Males and Females, with estimated p-values for the test of departure from HWE computed via Markov Chain Monte Carlo (MCMC).

| | Males Observed | Males Expected | Females Observed | Females Expected |
|---|---|---|---|---|
| N|N | 88 (57.5) | 91.8 | 97 (62.6) | 94.5 |
| N|M1 | 24 (15.7) | 20.9 | 21 (13.5) | 17.2 |
| M1|M1 | 0 (0) | 1.2 | 0 (0) | 0.8 |
| N|M2, M1|M2 | 40 (26.1) | 36.2 | 28 (18.1) | 39.2 |
| M2|M2 | 1 (0.7) | 2.9 | 9 (5.8) | 3.4 |
| Total | 153 (100) | 153 | 155 (100) | 155 |
| Estimated P-value | NS | | 0.00517 | |
| P-value Std Error | 0.0001 | | 0.0000 | |

NS = not statistically significant.
Note Values are number (percentage)

The genotype frequencies of ANXA5 gene promoter haplotypes in IVF couples included in the current study and two different control groups are shown in Table 3. The abundance of the M2 haplotype was enriched in both male and female IVF patients compared to both the Muenster controls (female) and the PopGen controls (male and female).

TABLE 3

Genotype Frequencies of ANXA5 Gene Promoter Haplotypes in UK IVF Couples & Two Different Control Groups

| | IVF Male and Female patients | | | | Muenster Fertile Controls[a] | | PopGen[b] | |
|---|---|---|---|---|---|---|---|---|
| | Males | Males | Females | Females | Female | | Male & Female | |
| Controls | Observed | Expected | Observed | Expected | Observed | Expected | Observed | Expected |
| N|N | 88 (57.5) | 91.8 | 97 (62.6) | 94.5 | 356 (71.2) | 343.6 | 415 (77.9) | 413.3 |
| N|M1 | 24 (15.7) | 20.9 | 21 (13.5) | 17.2 | 87 (17.4) | 99.5 | 35 (6.6) | 47.8 |
| M1|M1 | 0 (0) | 1.2 | 0 (0) | 0.8 | 16 (3.2) | 7.2 | 1 (0.2) | 1.5 |
| N|M2, M1|M2 | 40 (26.1) | 36.2 | 28 (18.1) | 39.2 | 31 (6.2) | 48.4 | 77 (14.4) | 69.0 |
| M2|M2 | 1 (0.7) | 2.9 | 9 (5.8) | 3.4 | 10 (2.0) | 1.4 | 5 (0.9) | 1.4 |
| Total | 153 (100) | 153 | 155 (100) | 155 | 500 | 500 | 533 | 533 |

Note

Values are number (percentage)

Expected values correspond to those expected under Hardy-Weinberg equilibrium

The IVF female patients were not in HWE (p=0.0052) owing to the excess of M2 heterozygotes but particularly M2 homozygotes (9 observed v.3.4 expected). To check whether the significant deviation from HWE observed in the female subgroup could be attributed to chance we subsampled 155 individuals at random from the entire set (males and females combined) and estimated the p-value for deviation from HWE using the same method and recorded the p-value. We performed this procedure 1000 times, and of these only three p-values recorded were more extreme than those observed for the all-female group, thus suggesting that the deviation from HWE in females is real and not attributable to chance The patients' previous IVF, IUI and pregnancy histories are shown in Table 4. The numbers of previous failed IVF cycles were highest in couples who had one partner a homozygote and one non-carrier (mean 3.1 previous IVF) and in couples where the male partner was a carrier (mean 2.1 previous IVF).

TABLE 4

Patients' Previous IVF and IUI Cycles and Pregnancy Histories

| Classification | Couples | IVF cycles | IUI | Pregnancies | Total miscarriages | Live births | Time of last miscarriage (gestational weeks)[a] |
|---|---|---|---|---|---|---|---|
| Couples (1 or both partners a M2 carrier or homozygote) | 69 | (2.0) 191 | 23 | (0.9) 63 | (0.7) 50 | 4 | (10.1, 5-23) (n = 17) |
| Male only carrier | 31 | (2.1) 66 | 3 | (1.1) 33 | (0.8) 26 | 1 | (9.6, 7-22) (n = 11) |
| Female only carrier | 22 | (1.6) 36 | 12 (all same patient) | (0.8) 17 | (0.7) 15 | 2 | 23 |
| Homozygous partner (6 female 1 male) and non-carrier partner | 7 | (3.1) 22 | 3 | (1.3) 9 (1 female had 4) | 6 (1 female had 4, 1 female had 2) | 0 | 5, 9 |
| Both partners carriers | 6 | (1.9) 17 | 5 | (0.6) 5 | 3 | 1 | 6, 7, 15 |
| 1 partner homozygote, 1 partner carrier | 3 | (1.7) 5 | 0 | 3 | 3 | 0 | 7, 15, very early |
| Non-carrier couples | 88 | (1.9) 153 | (0.2) 12 | (0.9) 83 | (0.6) 53 | 13 | 9 weeks, 5-26 n = 25 |

* Pregnancy Loss
Note
values are numbers, (mean) or (mean, range).

Previous live births were very low in all carrier/homozygous groups (range 0-4) and a slightly higher incidence was observed in non-carrier couples (N=13). The patients' most recently reported miscarriage in carrier couples occurred at a mean of 10.1 weeks (range 5 to 23 weeks) in the 17 miscarriages where date of loss was reported. In non-carrier couples miscarriage (N=53) occurred at a mean of 9 weeks (range 5-26) in the 25 of 53 miscarriages.

Example 5

Male Infertility and M2 Carriage Frequency

Overall 63 of 157 males (40%) had associated infertility factors. Carriage incidence in this group was 27% (N=17). Overall, oligospermia was the most frequent finding (40% N=25 of the infertile males) followed by oligoasthenoteratozoospermia (OATS—13% N=8 of the infertile males).

Of 157 female patients, 93 (59%) had a diagnosis of infertility other than unexplained or male factor. Additionally, 25 of the 93 (27%) with a diagnosis were also found to be M2 carriers. Unexplained, poor ovarian reserve/ovulation failure often linked to age, plus PCOS are the most frequently cited causes of infertility in both groups. However, male infertility is cited as the primary cause of infertility in the couple in 21% of the non-carrier group but noted in only 1 of the group of 37 patients who carried the M2 haplotype. Six out of 17 PCOS cases (35%) were also carriers.

Example 6

Unexplained Infertility and M2 Carriage Frequency 104 patients (33%) presented as having no explanation for infertility. Of these, 38 patients (37%) were identified as M2 carriers; 25 male (24%) and 13 female (13%). There were 9 female homozygotes (6% of all females). There was also one male homozygote aged 49 for whom the couple had no other known diagnosis although his female partner had had 2 IVF cycles which had resulted in miscarriage.

Example 7

Preliminary Results

Carriership of the haplotype M2/ANXA5 in this cohort of patient couples was 44%, representing a very high incidence. Furthermore it was present in 27% of male infertility patients, 27% of female infertility patients and in 37% of patients with previously unexplained reasons for infertility. Of the patients who carried the M2 haplotype in the present study, none tested positive for APS. Genotype M1/M1 was absent in the RPL cohort and rare in controls. Genotype M1/M2 was not observed in the recurrent pregnancy loss cohort and seen only in a total of 8 from control groups and in only 4 patients in this IVF cohort. However the incidence of homozygote M2 female patients was elevated at 6% in this cohort and one male M2 homozygote was recorded.

Female homozygote frequency was three times higher than that reported from other control groups and double that of recurrent pregnancy loss females (Rogenhofer et al 2012).

We justify the use of the PopGen and Muenster controls as Nelis et al (2009) concluded that four areas could be identified namely 1) Central and Western Europe, 2) the Baltic countries, Poland and Western Russia, 3) Finland, and 4) Italy, which if not corrected for the interpopulation differences would affect the significance of disease gene associations. The incidence in controls from published studies from Germany, Southern Italy and Bulgaria—representative of three of these regions—have all shown consistency in the M2 haplotype frequency. The majority of the IVF patients were White British (77% males 75% females), which correspond to the Central and Western Europe region. We had no Finnish patients and analysis with and without the subset of Indian/Pakistani and others still showed the significant departure from HWE in females but not in males mainly due to the abundance of M2 homozygotes.

In terms of ethnicity we found M2 carriers in a wide range of ethnicities including Jewish, Turkish and Middle East patients in addition to Indian and Pakistani patients. The possible differences in carriage rate and clinical effects in these ethnicities warrants further investigation since there may be significant differences in incidence and pathology. The incidence in the Caucasian populations of Europe is well established (Markoff et al, 2011) and Myamura et al (2011) reported that carriage of the haplotype resulted in similar risks for recurrent pregnancy loss in the Japanese population as that observed in the populations of central Europe; but the population incidence is lower (5.5 versus 15%). Thus further study of different ethnicities other than white Europeans and Japanese is warranted.

Any impairment of embryonic coagulation is of particular importance in IVF practice since the focus is often on managing and providing for healthy gametes and embryos, selecting for optimal embryo viability and ensuring a healthy uterus able to sustain a pregnancy. However, although the largest single cause of miscarriage is believed to be the aneuploid embryo, other factors are clearly of significance, especially in RPL cases, where it can remain an issue even after the transfer of euploid embryos following IVF. The relatively recently discovered genetic factor M2/ANXA5 is alone in influencing placental function via adverse effects on embryonic anticoagulation and if undetected could negate the considerable work and cost incurred to establish a healthy pregnancy via IVF. In our study there were a significant number of patients equally distributed between male and female where M2 carriage was either an additional factor to those already determined, or it was present in a significant number of patients with no other infertility diagnosis. There is a growing body of evidence of the risks of carriage of the M2/ANXA5 haplotype to maternal health (RPL, VTE, PE, GH APS: Tiscia et al, 2009; Grandone et al, 2010; Bogdanova et al, 2012). Bogdanova et al (2012) postulate that carriage of the M2/ANXA 5 haplotype leads to a reduced ANXA5 cover of exposed phosphatidylserine surfaces, and this reduced shielding would allow coagulation factors to compete for phospholipid binding. Secondly, there would be greater exposure of phospholipid antigenic factors that would then lead to aPA development which in turn would further disrupt the ANXA5 shield. Sifakis et al (2010) demonstrated significant differences in mRNA expression between normal and FGR pregnancies but no differences in ANXA5 protein levels. However, the authors did not genotype their samples for M2/ANXA5.

Additionally, the identification of a subset of patients before IVF treatment that are ANXA5 carriers is important since from this study their IVF cycle failure rate is higher than for non-carriers. We report here a single male homozygous patient with no other infertility diagnosis whose female partner had had 2 previous failed IVF cycles. Thus identifying and treating female patients who are themselves M2 carriers or whose male partner is a carrier may assist in reducing the incidence of small for gestational age (SGA) by mitigating the adverse effects on embryonic anticoagulation.

Since the defect is conveyed embryonally and affects embryonic anticoagulation and the risk is independent of any specific parental transmission, that is, it can be embryonally induced if the transmission is either maternal or paternal (or both), screening of both partners presenting for IVF for carriage of the M2/ANXA5 haplotype ought to be considered as routine and early in the diagnostic work up of the couple being treated with their own gametes. The M2 haplotype appears to be an additional independent factor that contributes to the risk of pregnancy failure.

Example 8

Initial Outcome Data for M2 Haplotype Patients Treated with LMWH

Patients were tested for the M2 haplotype and placed into two groups. One group, termed "treated," consisted of 63 patients. These patients were both tested for the M2 haplotype carrier status and were treated with LMWH at the time of embryo transfer. The second group, termed "untreated," comprised 62 patients and they were tested for the M2 haplotype but not treated with LMWH. In comparing the treated and untreated groups, the untreated group was one full year younger (35) than the treated (36.1), and the untreated also had infertility for one full year less (4.24) than the treated group (5.24). See Table 5. In addition, 15 patients in the treated group had time lapse embryo culture, known as embryoscope, while only 1 patient in the untreated group had an embryoscope. The treated group also had 7 of the 15 patients with embryo time lapse culture progress to clinical pregnancy and live birth. However, both groups shared two characteristics. First, the untreated group had an average of 0.38 previous miscarriages, and the treated group had an average of 0.52 previous miscarriages. Second, the untreated group had an average of 2.7 previous IVF cycles, and the treated group had an average of 2.6 previous IVF cycles. Even with the aforementioned minimal differences and close similarities, the treated group had an elevated live birth rate of 38% compared to the global average of 30-35%, while none of the patients (0%) of the untreated group achieved a live birth.

TABLE 5

Preliminary Outcome Data

| | ANXA5 M2 Treated Patients M2 positive and treated with heparin | | M2 Untreated Patients M2 positive but who had an IVF treatment before tested and therefore NO heparin | |
|---|---|---|---|---|
| Sample Size (n) | 63 | | 42 | |
| Mean # Previous IVF Treatments | 2.60 | | 2.7 | |
| Last Treatment Clinical Pregnancy Event Count | 28 (44.4%) | | | |
| Ongoing pregnancy (>24 weeks) | 9 | | | |
| Deliveries | 15 (23.8%) | | | |
| Ongoing (>22 wks)/LB | 24 (38% CP/LBR) | | | |
| Last Treatment Miscarriages Count | 4 (14%) | | | |
| Mean age (at date of treatment) | 36.13 | | 35.0 | |
| Average previous miscarriages | 0.52 | | 0.38 | |
| Average years infertile | 5.24 | | 4.24 | |
| No of patients with embryos transferred | 63 | | 38 | 90.5% |
| Total embryos transferred | 104 | | 59 | Mean age 34.9 (Mean age NOT pregnant 34.9) |
| Mean embryos per patient | 1.65 | | 1.4 | |
| Total with embryoscope | 15 | 23.8% | 1 | 2.6% |
| Total with blastocyst transfer | 15 | 23.8% | 9 | 23.7% |
| Positive pregnancy test | 35 | 35/63 = 55.6% | 15 | 15/38 = 39.5% |
| Biochemical pregnancies as an endpoint | 7 | Incidence (7/63 positive pregnancy tests (11%) | 8 | Incidence (8/38 positive pregnancy tests 21%) |
| Clinical Pregnancy (CP) | 28 | 28/63 = 44.4% | 7 | 7/38 = 18.4% |
| Implantation Rate | 55.6% | 35/63 = 55.6% | 39.4% | 15/38 = 39.4% |
| Miscarriage | 4 | 4/63 = 6.3% | 7 | 7/38 = 18.4% |
| Live Births to date (August 2014) | 15 | 15/63 = 38% | 0 | 0/38 = 0% |

Thus, it is believed that mothers treated with an anticoagulant (preferably, LMWH) where either the mother or father are carriers for the M2 haplotype, will have improved clinical pregnancy rates and/or improved live birth rates. In preferred embodiments, the mother is treated at the time, or very close to, or shortly after, the time of embryo transfer. LMWH is administered for at least 4 weeks, for at least 8 weeks, for at least 12 weeks, or for at least 16 weeks. Treatment with an anticoagulant, such as LMWH, has the ability to increase the chance of clinical pregnancy, and/or decrease the rate of miscarriage and thereby increase the chance of live birth. Our results are in direct contrast to the results obtained by Rodgers. Moreover treatment with an anticoagulant, such as LMWH, may be used to increase the rates of successful pregnancies and/or live births in mothers undergoing in vitro fertilization.

It is expected that patients where both partners are carriers for M2 haplotypes would benefit the most with the treatment of an anticoagulant, such as LMWH, prior to, simultaneously, and/or within weeks of becoming pregnant.

TABLE 6

| SUBGROUP OF BOTH PARTNERS CARRIERS/ HOMOZYGOTE AND TREATED WITH HEPARIN (N) | | |
|---|---|---|
| Sample Size | 8 | |
| Mean previous IVF treatments | 2.9 | |
| Mean age (at date of treatment) | 34.95 | |
| No with one or more Foetal Heart beat (FH) | 3 | |
| Average Previous miscarriages | 0 | |
| Average years infertile | 6.6 | larger time period |
| Number with live birth | 3 (37.5%) | |

Example 9

Statistical Analysis of the Outcome Data for M2 Haplotype Patients Treated with LMWH Final outcome data was statistically analysed for 125 patients with an embryo transfer who were broken into two study groups; 63 (50.4%) patients in a test/treatment group and 62 (49.6%) in a yardstick (or control) group. The final data extended the results reported above for the interim analysis. Not only did the data set include information on pregnancy outcomes, but additional variables were recorded summarising the patients' demographics and treatment histories. The analysis of this data set focuses on three endpoints specified: live births; clinical miscarriages; and successful implantations.

The definitions of the three endpoints analysed are as follows:

The live births endpoint is a binary variable indicating whether the embryo transfer resulted in a live birth or not. All patients with an embryo transfer were included in the analysis of the live births endpoint.

Clinical miscarriage is a binary variable indicating whether the embryo transfer resulted in a clinical miscarriage or a live birth. Only those patients that reached the clinical pregnancy stage (i.e., where an ultrasound scan detected a foetal heart rate) were included in the analysis of clinical miscarriage.

For each patient with an embryo transfer, one, two or three embryos were transferred into the patient. The implantation incidence rate is then defined as the number of foetal heart rates detected divided by the number of embryos transferred. The implantation incidence rate was converted to a successful implantation endpoint prior to analysis. The successful implantation endpoint is a binary variable indicating whether the implantation was a success or failure (i.e., foetal heart rate detected or not) for each embryo transferred. Each embryo transferred was included in the analysis of successful implantation In addition to study group (treatment/control), the following independent variables (patient demographics and treatment histories) were also studied to determine whether there is an association between the independent variables and with the three endpoints defined above.

Patient Age

M2 Haplotype Results (Female and Male).

M2 haplotype results were obtained for both the patient (female) and their partner (male). Following the grouping convention applied in Fishel, et al. (2014) these were categorised as follows:

Both carriers;
Male carrier only;
Female carrier only;
One homozygote, one carrier; and
One homozygote only.

It was found that there were few patients in the 'One homozygote, one carrier' (8 observations) and 'One homozygote only' (4 observations) categories and therefore regrouped these into a single homozygote category ('One homozygote only or one homozygote/one carrier').

Number of Embryos Transferred.

This variable was grouped into two categories: one for those embryo transfers with 1 embryo transferred; and one for those embryo transfers with 2 or 3 embryos transferred.

Type of Incubator

Duration of Infertility (Years)

Number of Previous IVF Cycles:

This variable was grouped into five categories depending upon whether the patient had 0, 1, 2, 3, or 4 or more previous IVF cycles.

Number of Previous Miscarriages:

This variable was grouped into three categories depending upon whether the patient had 0, 1, or 2 or more previous miscarriages.

Embryo Transfer:

For each embryo transferred, the type of embryo was recorded. These were recorded as: morula, blastocyst, or the number of cells transferred. Given the large number of categories observed, a single variable was created, grouping the embryo transfers into those that were blastocyst transfers and those that were not. Since blastocyst transfers were consistent across embryos within a transfer, only a single variable is needed (regardless of the number of embryos transferred).

Use of Intralipids:

Thirty-three embryo transfers in the treatment group were associated with patients receiving intralipids. It was determined that for the majority of cases these patients were given intralipids because they had immunological problems and that this was more likely to be associated with pregnancy outcomes. Therefore, these patients were grouped into those who were treated with intralipids for immunological problems and those who were not. Two patients were identified as receiving intralipids for no clinical reason (two patients) and were therefore not included in the 'Treated with intralipids for immunological problems' category.

Donor Egg Use

For each endpoint, individual tests of association (via univariate regression models) were carried out with the independent variables in order to assess their statistical significance as individual predictors of the outcome. All three of the endpoints analysed are binary variables. In this case, a logistic regression model is appropriate, which uses a logistic transformation to express the probability of the outcome (e.g., live birth) as a linear function of the independent variables.

Following the univariate tests, a multiple logistic regression model is applied to assess the collective predictive accuracy of the independent variables for the outcome. This allows for the investigation of the potential effect of study group on the chance of having each outcome and also account for (and estimate the effects of) the other independent variables.

Only those variables that are found to be statistically significant in the univariate analysis (for at least one odds ratio with a 10% significance level, i.e. requiring the probability that the observed effect is due to chance alone is less than 10%) are considered for inclusion in this multiple variable model.

For the multiple logistic regression modelling, a backward stepwise regression algorithm, which begins with the model including all independent variables that were identified as significant from the univariate tests, and then successively removes them from the model in order to determine the model that provides the best fit was used. The model fit is determined using likelihood ratio tests (with a 5% significance level, i.e., requiring the probability that the observed effect is due to chance alone is less than 5%) ensuring that only variables that have a substantial effect on the performance of the final model are included.

Out of the 125 patients with an embryo transfer recorded, there were 34 patients who provided an observation in both study groups. This means there were patients who underwent IVF twice in the study, once without the study treatment and once with the treatment. The multiple pregnancy outcomes for these patients are not independent and therefore cannot be treated as such within the statistical model. To account for the repeated nature of the data (multiple observations per patient), logistic mixed-effects models are applied, including a random effect for each patient in order to model the correlation among their multiple responses.

Separation was also identified in a number of instances. Separation occurs in logistic regression when the binary outcome can be separated by an independent variable. Complete separation occurs when the separation is perfect whereas quasi-complete separation happens when the outcome is separated to a certain degree, for example where all of the responses for one factor of a categorical variable (rather than all factors) have the same outcome (Heinze & Schemper, 2002). As described below, in this study live births only occurred in patients within the treatment group and not at all in the control group. Thus, the binary outcome 'live birth' is separated by the independent variable, 'study group'. Similarly, all patients in the control group that reached the clinical pregnancy stage had clinical miscarriages and so 'clinical miscarriage' is also separated by the independent variable, 'study group'.

In the presence of separation, standard logistic regression models fitted via maximum likelihood can produce infinite or biased estimates. Separation is a common problem in logistic regression and is more likely to occur with smaller sample sizes, with more dichotomous covariates, and with more extreme odds ratios and with larger imbalances in their distribution.

There are a few options for dealing with this in the analysis. Firstly, those cases causing separation could be omitted from the analysis. However, this would not be appropriate in this case as it would mean that information about the effect of this important independent variable would not exist and also it would not allow for the adjustment of the effects of the other independent variables for the effect of this variable. Furthermore, this would mean throwing away data, reducing the predictive power of the modelling.

Therefore, two other alternatives are either application of Firth's bias reducing, penalised maximum likelihood logistic regression (Fisher, 1992, 1993) or a Bayesian logistic mixed-effect model (Fong, et al., 2010; Zhao, et al., 2006). In this instance the latter was chosen, for the Bayesian approach provided a more flexible framework that to deal with the separation issue but also to include a random effect in the model to account for the repeated observations from some patients, as discussed above. It's not possible to incorporate random effects within Firth's logistic regression model. Using a Bayesian logistic mixed-effect model does require specifying prior distributions for the fixed and random effects. In this case, with no other information available, a Normal distribution was chosen for the fixed effects and the default flat prior for the random effects.

The successful implantation endpoint did not exhibit separation with any of the independent variables considered. However, for consistency with the other outcomes, Bayesian logistic mixed-effect modelling was also used for this endpoint. A more standard approach in this case would have been a standard logistic mixed-effect analysis. The analysis was re-run using this approach and found that it produced consistent results with the Bayesian model.

All analyses were performed in the statistical software package R version 3.1.1 (R Core Team, 2013). The bglmer function in the blme package was used to implement the Bayesian logistic mixed-effect modelling (Dorie, 2014).

Live Births

As shown in Table 7, the pregnancy outcomes of the 125 patients with an embryo transfer recorded in the study split by study group. Of the 125 patients with an embryo transfer recorded, surprisingly 25/63 (39.7%) within the treatment group resulted in a live birth and none (out of 62) in the control group. The data shows that the odds of a successful live birth are estimated to be approximately 56 times higher (OR=56.08; 95% CI: 4.95, 635.64) for patients in the treatment group compared with the control group ($p=0.0012$).

TABLE 7

Pregnancy outcomes for patients with an embryo transfer, by study group.

| Study Group | Treatment | Control |
| --- | --- | --- |
| Patients with an embryo transfer | 63 | 62 |
| Number of embryos transferred | 104 | 95 |
| Patients with biochemical pregnancies (positive pregnancy tests) | 35 | 23 |
| Patients without biochemical pregnancies (negative pregnancy tests; loss pre-implantation) | 28 | 39 |
| Number of foetal heart rates detected | 36 | 12 |
| Patients with clinical pregnancies (foetal heart rate detected) | 28 | 12 |
| Patients without clinical pregnancies | 35 | 50 |
| Patients with a biochemical loss (biochemical pregnancies but no foetal heart rate detected) | 7 | 11 |
| Patients with clinical miscarriages (miscarriages after foetal heart rate detected) | 3 | 12 |
| Patients with live births | 25 | 0 |
| Patients with no live births | 38 | 62 |

Moreover, the odds of a successful live birth are estimated to be 2.7 times higher (OR=2.69; 95% CI: 1.00, 7.23) for embryo transfers where two or more embryos were transferred compared with embryo transfers where one embryo was transferred ($p=0.050$).

TABLE 8

Cross-tabulation of live births versus number of embryos transferred, n (column %).

| | No. Embryos Transferred | |
| --- | --- | --- |
| | 1 | 2/3 |
| Patients with live births | 6 (11.3) | 19 (26.4) |
| Patients with no live births | 47 (88.7) | 53 (73.6) |
| Total | 53 (100) | 72 (100) |

Additionally, the number of previous IVF cycles was positively correlated with the odds of a successful live birth. The odds were estimated to be 4 times higher (OR=4.04; 95% CI: 0.89, 18.37) for patients with two previous rounds compared to none ($p=0.0711$); and 7.5 times higher (OR=7.46, 95% confidence interval: 1.66, 33.55) for patients with three previous rounds compared to none ($p=0.0088$).

TABLE 9

Cross-tabulation of live births versus previous IVF cycles, n (column %).

| | Previous IVF Cycles | | | | |
| --- | --- | --- | --- | --- | --- |
| | 0 | 1 | 2 | 3 | 4+ |
| Patients with live births | 2 (5.9) | 6 (19.4) | 7 (26.9) | 9 (40.9) | 1 (8.3) |
| Patients with no live births | 32 (94.1) | 25 (80.6) | 19 (73.1) | 13 (59.1) | 11 (91.7) |
| Total | 34 (100) | 31 (100) | 26 (100) | 22 (100) | 12 (100) |

Furthermore, the odds of a successful live birth are also estimated to be 2.4 times higher (OR=2.37, 95% CI: 0.91, 6.15) for patients with one previous miscarriage compared to none ($p=0.0773$).

TABLE 10

Cross-tabulation of live births versus previous miscarriages, n (column %).

| | Previous Miscarriages | | |
| --- | --- | --- | --- |
| | 0 | 1 | 2+ |
| Patients with live births | 12 (14.3) | 10 (29.4) | 3 (42.9) |
| Patients with no live births | 72 (85.7) | 24 (70.6) | 4 (57.1) |
| Total | 84 (100) | 34 (100) | 7 (100) |

The use of intralipids (due to immunological problems) was associated with 3 times the odds (OR=3.02, 95% CI: 1.19, 7.64) of a successful live birth compared to a patient not on intralipids ($p=0.0199$). As shown in Table 11, the proportion of patients with a live birth for those using intralipids (due to immunological problems) was 35.5%, compared with 14.9% for those not using intralipids. However, all of those patients on intralipids were in the treatment group. Looking at only those patients in the treatment group, also shown in Table 11, these proportions become: 35.5% versus 43.8%, respectively.

TABLE 11

| | Intralipid Use (due to immunological problems) | Yes (%) | No (%) |
|---|---|---|---|
| Cross-tabulation of live births versus intralipid use due to immunological problems, n (column %). | Patients with live births | 11 (35.5) | 14 (14.9) |
| | Patients with no live births | 20 (64.5) | 80 (85.1) |
| | Total | 31 (100) | 94 (100) |
| Cross-tabulation of live births versus intraplid use due to immunological problems, n (column %), for patients in the treatment group only. | Patients with live births | 11 (35.5) | 14 (43.8) |
| | Patients with no live births | 20 (64.5) | 18 (56.3) |
| | Total | 31 (100) | 32 (100) |

Donor egg use was associated with 4 times the odds (OR=4.03, 95% CI: 0.93, 17.46) of a successful live birth compared to a patient not using a donor egg (p=0.0622).

TABLE 12

Cross-tabulation of live births versus Donor egg use, n (column %).

| Donor Egg Use | Yes | No |
|---|---|---|
| Patients with live births | 4 (50.0) | 21 (17.9) |
| Patients with no live births | 4 (50.0) | 96 (82.1) |
| Total | 8 (100) | 117 (100) |

Donor egg use was associated with 4 times the odds (OR=4.03, 95% CI: 0.93, 17.46) of a successful live birth compared to a patient not using a donor egg (p=0.0622).

Hence, the data suggest that the study group (e.g., treatment at embryo transfer/implantation with low molecular weight heparin) is a statistically significant predictor for live births, with the odds of a live birth estimated to be approximately 56 times higher for patients in the test/treatment group compared to the control group (OR=56.08; 95% CI: 4.95, 635.64; p=0.0012). If the odds of a live birth in the control group were 1 to 89 (i.e., p=1/90=1.11% and 1-p=89/90=98.89%; based on the model estimated odds), with OR=56, the odds of a live birth for the treatment group would be 56 times as good or approximately 1 to 1.59 (i.e., p=34.7/90=38.6% and 1-p=55.3/90=61.4%). So, on average, for every pregnancy in the control group that results in a successful pregnancy, 89 will not, but for every pregnancy in the treatment group that results in a successfully pregnancy, only 1.59 on average will not.

Clinical Miscarriages

Of the 40 patients with an embryo transfer that reached the clinical pregnancy stage (i.e., foetal heart rate detected on an ultrasound scan), 12/12 (100%) of those in the control group resulted in a clinical miscarriage and 3/28 (10.7%) of those in the treatment group. The odds of a clinical miscarriage are estimated to be 0.01 times (i.e., 99%) lower (OR=0.010; 95% CI: 0.001, 0.135) for patients in the treatment group compared with the control group (p=0.0005).

TABLE 13

Cross-tabulation of clinical miscarriages versus study group, n (column %).

| Study Group | Treatment | Control |
|---|---|---|
| Patients with live births | 25 (89.3) | 0 (0) |
| Patients with clinical miscarriages | 3 (10.7) | 12 (100) |
| Total | 28 (100) | 12 (100) |

Hence, the data suggest that study group (e.g., treatment with low molecular weight heparin) is a statistically significant predictor for clinical miscarriage (given clinical pregnancy, i.e., foetal heart rate detected), with the odds of a clinical miscarriage estimated to be 0.01 times (i.e., 99%) lower for patients in the test/treatment group compared to the yardstick group (OR=0.010; 95% CI: 0.00079, 0.135; p=0.0005).

Successful Implantation

Of the 199 embryos transferred, 36/104 (34.6%) of those in the treatment group resulted in a successful implantation (foetal heart rate detected) and 12/95 (12.6%) of those in the control group. Thus, the odds of a successful implantation are estimated to be 4.1 times greater (OR=4.08; 95% CI: 1.85, 8.97) for embryo transfers in the treatment group compared with the control group (p=0.0005).

TABLE 14

Cross-tabulation of successful implantation versus study group, n (column %).

| Study Group | Treatment | Control |
|---|---|---|
| Embryos transferred with foetal heart rate detected | 36 (34.6) | 12 (12.6) |
| Embryos transferred with foetal heart rate not detected | 68 (65.4) | 83 (87.4) |
| Total | 104 (100) | 95 (100) |

Hence, the data suggest that study group is a statistically significant predictor for successful implantation (i.e., foetal heart rate detected, given embryo implanted), with the odds of successful implantation estimated to be approximately 4 times higher for patients in the test/treatment group compared to the control group (OR=4.08; 95% CI: 1.85, 8.97; p=0.0005).

REFERENCES

Bick, R. L., 2000. DRW Metroplex Recurrent Miscarriage Syndrome Cooperative Group. Recurrent Miscarriage Syndrome Due To Blood Coagulation Protein/Platelet Defects: Prevalence, Treatment And Outcome Results. Clin Appl Thromb Hemost 6, 115-125.

Bogdanova, N., Horst, J., Chlystun, M., Croucher, P. J., Nebel, A., Bohring, A.Todorova, A., Schreiber, S., Gereke, V., Krawczak, M., Markoff, A, 2007. A common haplotype of the annexin A5 (ANXA5) gene promoter is associated with recurrent pregnancy loss. Hum Mol Genet 16, 573-578.

Bogdanova, N., Baleva, M., Kremensky, I., Markoff, A., 2012. The annexin A5 protective shield model revisited: inherited carriage of the M2/ANXA5 haplotype in placenta as a predisposing factor for the development of obstetric antiphospholipid antibodies. Lupus. 21, 796-798.

Chinni, E., Tiscia, G., Colaizzo, D., Vergura, P., Margaglione, M., Grandone, E., 2009. Annexin V expression in human placenta is influenced by the carriership of the common haplotype M2" Fertil. Steril. 91 (3), 940-942.

Chunilal, S. D., Bates, S. M., 2009. Venous thromboembolism in pregnancy: diagnosis, management and prevention. Thromb. Haemost. 101, 428-434.

Firth, D. (1992) Bias reduction, the Jeffreys prior and GLIM. Fahrmeir, L., Francis, B., Gilchrist, R., Tutz, G., editors. Advances in GLIM and Statistical Modelling. Springer.

Firth, D. (1993) Bias reduction of maximum likelihood estimates. Biometrika, 80:27-38.

Fishel, S., et al. (2014) Multicentre study of the clinical relevance of screening IVF patients for carrier status of the annexin A5 M2 haplotype. Reproductive BioMedicine Online, Volume 29, Issue 1, Pages 80-87.

Gerke, V., Creutz, C. E., Moss, S. E., 2005. Annexins: linking Ca2p signalling to membrane dynamics. Nat. Rev. Mol. Cel. Biol. 6, 449-461.

Grandone, E., Margaglione, M., 2003. Inherited thrombophilia and gestational vascular complications. Best Pract. Res. Clin. Haematol. 16, 321-332.

Grandone, E., Tiscia, G., Colaizzo, D., Chinni, E., Pisanelli, D., Bafunno, V., Margaglione, M., 2010. Role of the M2 haplotype within the annexin A5 gene in the occurrence of pregnancy-related venous thromboembolism. Am. J. Obstet. Gynecol. 203, 461, e1-5.

Guo, S. W. and Thompson, E. A. (1992) Performing the exact test of Hardy-Weinberg proportion for multiple alleles.Biometrics,48,361-372

Heinze, G. (1999): "The application of Firth's procedure to Cox and logistic regression", Technical Report 10/1999, Section for Clinical Biometrics, CeMSIIS, Medical University of Vienna.

Heinze, G., Schemper, M. (2002) A solution to the problem of separation in logistic regression. Statistics in medicine, 21:2409-2419.

Heinze, G., Ploner M. (2004). Technical Report 2/2004: A SAS-macro, S-PLUS library and R package to perform logistic regression without convergence problems. Section of Clinical Biometrics, Department of Medical Computer Sciences, Medical University of Vienna, Vienna, Austria. URL http://www.meduniwien.ac.at/user/georg.heinze/techreps/tr2_2004.pdf Henriksson, P., Westerlund, E., Wallen, H. Brandt, L., Hovatta, O., Ekbom, A., 2013. Incidence of pulmonary and venous thromboembolism in pregnancies after in vitro fertilisation: cross sectional study. BMJ. 346, e8632.

Krawczak, M., Nikolaus S, von Eberstein H, Croucher PJP, El Mokhtari N E, Schreiber, S, PoGen:population-based recruitment of patients and controls for the analysis of complex genotype-phenotype relationships. J. Commun Genet 2006; 9:55-61

Malassiné, A., Frendo, J-L., Evain-Brion, D., 2003 A comparison of placental development and endocrine functions between the human and mouse model Human Reproduction Update Vol. 9, No6 531-539

Markoff, A., Gerdes, S., Feldner, S., Bogdanova, N., Gerke, V., Grandone, E., 2010. Reduced allele specific annexin A5 mRNA levels in placentas carrying the M2/ANXA5 allele. *Placenta.* 31(10), 937-940.

Markoff, A., Bogdanova, N., Samama, M. M., 2011. Hereditary thrombophilic risk factors for recurrent pregnancy loss. Hered. Genet. 1, 103.

Miyamura, H., Nishizawa, H., Ota, S., Suzuki, M., Inagaki, A., Egusa, H., Nishiyama, S., Takema, K., Pryor-Koishi, K. Nakanishi, I., Fujita, T., Imayoshi, Y., Markoff, A., Yanagihara, I., Udagawa, Y., Kurahashi, H., et al., 2011. Polymorphisms in the annexin A5 gene promoter in Japanese women with recurrent pregnancy loss. Mol. Hum. Reprod. 17, 447-452.

Morgan, R. O., Bell, D. W., Testa, J. R., Fernandez, M. P., 1998. Genomic locations of ANX11 and ANX13 and the evolutionary genetics of human annexins. Genomics. 48, 100, e10.

Nelis M, Esko T, Mägi R, Zimprich F, Zimprich A, Toncheva, D., Karachanak, S. Piská čkova, T., Balaščák, I. Peltonen, L., Jakkula, E., Rehnström, K., Lathrop, M., Heath, S., Galan, P., Schreiber, S., Meitinger, T. Pfeufer, A Wichmann, H-E., Melegh, B., Polgár, N., Toniolo, D., Gasparini, P., D'Adamo, P., Klovins, J., Nikitina-Zake, L., Kučinskas, V., Kasnauskienė, J., Lubinski, J., Debniak, T., Limborska, S., Khrunin, A., Estivill, X. Rabionet, R. Marsal, S., Julià, A., Antonarakis, S. E., Deutsch, D., Borel, C. Attar, H., Gagnebin, M., Macek, M., Krawczak, M., Remm, M. Metspalu, A., et al. (2009) Genetic Structure of Europeans: A View from the North-East. PLoS ONE 4(5): e5472.doi:10.1371/journal.pone.0005472

Nelson, S. M., Greer, I. A., 2008. The potential role of heparin in assisted conception. Hum. Reprod. Update. 14 (6), 623-645.

Peduzzi, P., Concato, J., Kemper, E., Holford, E., and Feinstein, A. (1996) A simulation study of the number of events per variable in logistic regression analysis. Journal of Clinical Epidemiology, Volume 49, Issue 12, pp. 1373-1379.

Ploner M, Dunkler D, Southworth H, Heinze G (2013). logistf: Firth's bias reduced logistic regression. R package version 2.1. http://CRAN.R-project.org/package=logistf R Core Team (2013). R: A language and environment for statistical computing. R Foundation for Statistical Computing, Vienna, Austria. URL http://www.R-project.org/

Rand J. H. N, WuXX, Guller S, Scher, J, Andree H A, Lockwood C J. Antiphospholipid immunoglobulin G antibodies reduce annexin-V levels on syncytiotrophoblast apical membranes and in culture media of placental villi. Am J Obstet Gynecol 1997; 177:918-23

Rand, J. H. N., 1999. Engl. J. Med. 340, 1035-1036.

RCOG SAC opinion Paper 8, 2007.

RCOG Scientific Impact Paper 26 Jun. 2011

Rey, E., Kahn, S. R., David, M. Shrier, I., 2003. Thrombophilic disorders and fetal loss: a meta-analysis. Lancet. 361, 901-908.

Rodger, M. A., Betancourt, M. T., Clark, P., Lindqvist, P. G., Dizon-Townson, D. Said, J., Seligsohn, U., Carrier, M., Salomon, O., Greer, I. A. et al., 2010. The Association of Factor V Leiden and Prothrombin Gene Mutation and Placenta-Mediated Pregnancy Complications: A Systematic Review and Meta-analysis of Prospective Cohort Studies. PLoS Med 7(6): e1000292. doi:10.1371/journal.pmed.1000292

Rogenhofer, N., Engels, L., Bogdanova, N., Tiittelmann, F., Markoff, A., Thaler, C., 2012. Paternal and maternal carriage of the annexin A5 M2 haplotype are equal risk factors for recurrent pregnancy loss: a pilot study. Fertil. Steril. 98 (2), 383-388.

Rogenhofer N, Engels L, Bogdanova N, Tiittelmann F, Thaler C J, Markoff A., 2013 Independent association of the M2/ANXA5 haplotype with recurrent pregnancy loss (RPL) in PCOS patients. Metabolism. 2013 Mar. 14. doi:pii: S0026-0495(13)00052-8.

Romisch, J., Seiffge, D., Reiner, G., Paques, E. P., Heimburger, N., 1991. In-vivo antithrombotic potency of placenta protein 4 (annexin V). Thromb. Res. 61, 93-104.

Seshadri, S., Sunkara, S. K., Khalaf, Y., El-Toukhy, .T, Hamoda, H., 2012. Effect of heparin on the outcome of IVF treatment: a systematic review and meta-analysis. Reprod. Biomed. Online. 25, 572-584.

Sifakis, S., Soufla, G., Koukoura, O., Soulitzis, N., Koutroulakis, D., Maiz, N., Konstantinidou, A., Melissari, E., Spandidos, D. A., 2010. Decreased annexin A5 mRNA placental expression in pregnancies complicated by fetal growth restriction. Thromb. Res. 125, 326-331.

Thiagarajan, P., Tait, J., 1990. Binding of annexin V/placental anticoagulant protein Ito platelets. Evidence for phosphatidylserine exposure in the procoagulant response of activated platelets. J. Biol. Chem. 265, 17420-17423.

Tiscia, G., Colaizzo, D. S., Margaglione, M., Grandone, E., 2009. Haplotype M2 in the annexin A5 (ANXA5) gene and the occurrence of obstetric complications. Thromb. Haemost. 102 (2), 309-313.

Tiscia, G., Colaizzo, D., Favuzzi, G., Vergura, P., Martinelli, P., Margaglione, M., Grandone, E., 2012. The M2 haplotype in the ANXA5 gene is an independent risk factor for idiopathic small-for-gestational age newborns, Mol. Hum. Reprod. 18 (10), 510-513.

Toth, B., Vocke, F., Rogenhofer, N., Friese, K., Thaler, C. J., Lohse, P., 2008. Paternal thrombophilic gene mutations are not associated with recurrent miscarriage. Am. J. Reprod. Immunol. 60, 325-332.

Tüttelmann, F., Pavlik, R., Hecht, S., Bogdanova, N., Nothnage, 1.M., Balschun, T., Krawczak, M., Thaler, C., Markoff, A., 2012. M2/ANXA5 is a risk factor for recurrent pregnancy loss (RPL) in a population undergoing in vitro fertilisation. ESHG Poster session P04.04.

Tüttelmann, F., Ivanov, P Dietzel, C Sofroniou, A. Tsvyatkovska T. M. Komsa-Penkova R. S, .Markoff, A Ueki H, Mizushina T, Laoharatchatathanin T, Terashima R, Nishimura Y, Rieanrakwong D, Yonezawa T, Kurusu S, Hasegawa Y, Brachvogel B, P6schl E, Kawaminami M,2012 Loss of maternal annexin A5 increases the likelihood of placental platelet thrombosis and foetal loss. Sci Rep. 2:827.; doi: 10.1038/srep00827. Epub 2012 Nov. 9.

Vincent Dorie (2014). blme: Bayesian Linear Mixed-Effects Models. R package version 1.0-2. http://CRAN.R-project.org/package=blme Vittinghoff, E. and McCulloch, C. (2006) Relaxing the Rule of Ten Events per Variable in Logistic and Cox Regression. American Journal of Epidemiology, Volume 165, Issue 6, pp. 710-718.

Wieacker, P Bogdanova, N., 2013 Further insights into the role of the annexin A5 M2 haplotype as recurrent pregnancy loss factor, assessing timing of miscarriage and partner risk Fertil.Steril; In Press http://dx.doi.org/10.1016/j.fertnstert.2013.06.046

Y. Fong, H. Rue and J. Wakefield. (2010) Bayesian inference for generalized linear mixed models. Biostatistics,11, 3, pp. 397-412

Younis, J. S., Samueloff, A., 2003. Gestational vascular complications. Best Pract. Res. Clin. Haematol. 16, 135-151.

Y. Zhao, J. Staudenmayer, B. A. Coull and M. P. Wand. (2006) General Design Bayesian Generalized Linear Mixed Models. Statistical Science, Vol. 21, No. 1, 35-51.

What is claimed:

1. A method of treating a M2 haplotype pregnancy, comprising
   (a) detecting or having detected in a sample a M2 haplotype pregnancy, wherein said M2 haplotype pregnancy exists when either the biological mother and/or the biological father is a carrier of the ANXA5 M2 haplotype, wherein both mother and father have undergone genetic testing to determine their individual M2 haplotype status, and wherein said mother suffers from recurrent pregnancy loss (RPL); and
   (b) administering to the mother of said M2 haplotype pregnancy an effective amount of an anticoagulant, wherein the anticoagulant is administered at a time selected from at least one of:
      (1) within 14 days prior to pregnancy; or
      (2) at the time of implantation; or
      (3) at the time of embryo transfer in in vitro fertilization.

2. The method of claim 1, wherein the anticoagulant is low molecular weight heparin ("LMWH").

3. The method of claim 1, wherein the anticoagulant is further administered:
   (a) every day throughout pregnancy until before delivery; and/or
   (b) for an additional 6 weeks after delivery.

4. The method of claim 1, wherein the mother has an increased risk of an obstetric complication.

5. The method of claim 4, wherein the obstetric complication is selected from at least one of recurrent pregnancy loss (RPL), in vitro fertilization (IVF) failure, implantation failure, foetal growth restriction (FGR), small for gestational age (SGA) newborn, intra-uterine foetal death (IUFD), gestational hypertension (GH), pre-eclampsia (PE) or venous thromboembolism (VTE).

6. The method of claim 1, wherein the method increases the rate of pregnancy.

7. The method of claim 1, wherein the mother is undergoing in vitro fertilization.

8. The method of claim 7, wherein the anticoagulant is low molecular weight heparin ("LMWH").

9. The method of claim 7, wherein the anticoagulant is further administered:
   (a) every day throughout pregnancy until before delivery; and/or
   (b) for an additional 6 weeks after delivery.

10. The method of claim 7, wherein the mother has an increased risk of an obstetric complication.

11. The method of claim 10, wherein the obstetric complication is selected from at least one of recurrent pregnancy loss (RPL), in vitro fertilization (IVF) failure, implantation failure, foetal growth restriction (FGR), small for gestational age (SGA) newborn, intra-uterine foetal death (IUFD), gestational hypertension (GH), pre-eclampsia (PE) or venous thromboembolism (VTE).

12. The method of claim 7, wherein the method increases the rate of pregnancy.

13. The method of claim 1, wherein both the biological mother and the biological father are a carrier of the ANXA5 M2 haplotype.

14. The method of claim 13, wherein the anticoagulant is low molecular weight heparin ("LMWH").

15. The method of claim 13, wherein the mother is undergoing in vitro fertilization.

16. The method of claim 13, wherein the anticoagulant is further administered:
   (a) every day throughout pregnancy until before delivery; and/or
   (b) for an additional 6 weeks after delivery.

17. The method of claim 13, wherein the mother has an increased risk of an obstetric complication.

18. The method of claim 17, wherein the obstetric complication is selected from at least one of recurrent pregnancy loss (RPL), in vitro fertilization (IVF) failure, implantation failure, foetal growth restriction (FGR), small for gestational age (SGA) newborn, intra-uterine foetal death (IUFD), gestational hypertension (GH), pre-eclampsia (PE) or venous thromboembolism (VTE).

19. The method of claim 13, wherein the method increases the rate of pregnancy.

20. The method of claim 1, wherein the ANXA5 M2 carrier status of said mother or father is determined by polymerase chain reaction ("PCR"), sequencing techniques, or the single nucleotide polymorphism detection technique established by IHG Pharmaco.

21. The method of claim 20, wherein the ANXA5 M2 carrier status is detected using a fluorescent molecule, an oligomer comprising at least 10 nucleotides, or a solid phase.

22. The method of claim 21, wherein the solid phase is a bead or a plate.

23. The method of claim 21, wherein the solid phase comprises plastic, silicon, glass, polystyrene, aluminium, steel, iron, copper, nickel, silver, gold, nitrocellulose or nylon.

24. The method of claim 21, wherein the oligomer having a length at least 15 nucleotides is used to detect the ANXA5 M2 haplotype.

25. The method of claim 20, wherein said sequencing technique utilizes Next Generation Sequencing techniques.

* * * * *

SEQUENCE LISTING

```
<160> NUMBER OF SEQ ID NOS: 5

<210> SEQ ID NO 1
<211> LENGTH: 496
<212> TYPE: DNA
<213> ORGANISM: Homo sapiens

<400> SEQUENCE: 1
ccgagccctg gacagctccc caggcccttc ccgcggcgcg aggacaagag gtctccgggg      60
ccctcggggg agcggcgcct cctcctggtt ccagcagctc tgcggccgct ccccacccag     120
gcccgcgaga ccagcgggac agtccgcgcc gcgggagacc aactgggacg agccgcgacc     180
cacgcaggcg cgctgaggcc ggggcagggg cgggcccggc tggcgcggcc ggcctgcggt     240
tggggccctg gcggggggtgg gacgggccaa gccgggcagg gccggggtgg ggccgctggc     300
gtttccgttg cttggatcag tctaggtgca gctgccggat ccttcagcgt ctgcatctcg     360
gcgtcgcccc gcgtaccgtc gcccggctct ccgccgctct cccgggggtt cggggcactt     420
gggtcccaca gtctgggtga gtggtcgcag cccggggagg gggctccttc tggagaggag     480
agcgtggtcg cggggc                                                    496

<210> SEQ ID NO 2
<211> LENGTH: 496
<212> TYPE: DNA
<213> ORGANISM: Homo sapiens

<400> SEQUENCE: 2
ccgagccctg gacagctccc caggcccttc ccgcggcgcg aggacaagag gtctccgggg      60
ccctcggggg agcggcgcct cctcctggtt ccagcagctc tgcggccgct ccccacccag     120
```

-continued

| | |
|---|---|
| gcccgcgaga ccagcgggac agtccgcgcc gcgggagacc aactgggacg agccgcgacc | 180 |
| cacgcaggcg cgctgaggcc ggggcagggg cgggcccggc tggcgcggcc ggcctgcggt | 240 |
| tgaggccctg gcggggtgg gccgggccaa gccgggcagg gccggggcgg ggccgctggc | 300 |
| gtttccgttg cttggatcag tctaggtgca gctgccagat ccttcagcgt ctgcatctcg | 360 |
| gcgtcgcccc gcgtaccgtc gcccggctct ccgccgctct ccggggggtt cggggcactt | 420 |
| gggtcccaca gtctgggtga gtggtcgcag cccggggagg gggctccttc tggagaggag | 480 |
| agcgtggtcg cggggc | 496 |

<210> SEQ ID NO 3
<211> LENGTH: 496
<212> TYPE: DNA
<213> ORGANISM: Homo sapiens

<400> SEQUENCE: 3

| | |
|---|---|
| ccgagccctg dacagctccc caggcccttc ccgcggcgcg aggacaagag gtctccgggg | 60 |
| ccctcggggg agcggcgcct cctcctggtt ccagcagctc tgcggccgct ccccacccag | 120 |
| gcccgcgaga ccagcgggac agtccgcgcc gcgggagacc aactgggacg agccgcgacc | 180 |
| cacgcaggcg cgctgaggcc ggggcagggg cgggcccggc tggcgcggcc ggcctgcggt | 240 |
| tgggccctg gcggggtgg gccgggccaa gccgggcagg gccggggcgg ggccgctggc | 300 |
| gtttccgttg cttggatcag tctaggtgca gctgccggat ccttcagcgt ctgcatctcg | 360 |
| gcgtcgcccc gcgtaccgtc gcccggctct ccgccgctct ccggggggtt cggggcactt | 420 |
| gggtcccaca gtctgggtga gtggtcgcag cccggggagg gggctccttc tggagaggag | 480 |
| agcgtggtcg cggggc | 496 |

<210> SEQ ID NO 4
<211> LENGTH: 22
<212> TYPE: DNA
<213> ORGANISM: Artificial Sequence
<220> FEATURE:
<223> OTHER INFORMATION: Forward Primer for PCR

<400> SEQUENCE: 4

| | |
|---|---|
| ccgagccctg gacagctccc ca | 22 |

<210> SEQ ID NO 5
<211> LENGTH: 20
<212> TYPE: DNA
<213> ORGANISM: Artificial Sequence
<220> FEATURE:
<223> OTHER INFORMATION: Reverse Primer for PCR

<400> SEQUENCE: 5

| | |
|---|---|
| ccagactgtg ggacccaagt | 20 |